United States Patent
Azadani et al.

(10) Patent No.: US 11,337,798 B2
(45) Date of Patent: May 24, 2022

(54) OPTIMIZATION OF REPLACEMENT HEART VALVE LEAFLETS

(71) Applicant: Colorado Seminary Which Owns and Operates the University of Denver, Denver, CO (US)

(72) Inventors: Ali Nejatbakhsh Azadani, Denver, CO (US); Mostafa Abbasi, Webster, NY (US)

(73) Assignee: Colorado Seminary Which Owns and Operates The University of Denver, Denver, CO (US)

( * ) Notice: Subject to any disclaimer, the term of this patent is extended or adjusted under 35 U.S.C. 154(b) by 263 days.

(21) Appl. No.: 16/706,485

(22) Filed: Dec. 6, 2019

(65) Prior Publication Data

US 2020/0188094 A1    Jun. 18, 2020

Related U.S. Application Data

(60) Provisional application No. 62/776,170, filed on Dec. 6, 2018.

(51) Int. Cl.
*A61F 2/24* (2006.01)
*G16H 50/50* (2018.01)
*A61L 27/36* (2006.01)

(52) U.S. Cl.
CPC ........ *A61F 2/2412* (2013.01); *A61L 27/3625* (2013.01); *G16H 50/50* (2018.01); *A61F 2240/001* (2013.01)

(58) Field of Classification Search
CPC ......... A61F 2/24; A61F 2/2496; A61F 2/2415
USPC .................................................. 623/2.1–2.19
See application file for complete search history.

(56) References Cited

U.S. PATENT DOCUMENTS

| | | | |
|---|---|---|---|
| 6,562,069 B2 | 5/2003 | Cai et al. | |
| 6,719,789 B2 | 4/2004 | Cox | |
| 8,219,229 B2 | 7/2012 | Cao et al. | |
| 9,232,996 B2 * | 1/2016 | Sun | A61F 2/2412 |

(Continued)

FOREIGN PATENT DOCUMENTS

WO    2018097902 A1    5/2018

OTHER PUBLICATIONS

Hsu et al., "Dynamic and Fluid-Structure Interaction Simulations of Bioprosthetic Heart Valves Using Parametric Design With T-Splines and Fung-Type Material Models", "Comput Mech", May 26, 2015, pp. 1211-1225, vol. 2015, No. 55, Publisher: Springer.

(Continued)

*Primary Examiner* — Suzette J Gherbi
(74) *Attorney, Agent, or Firm* — Neugeboren O'Dowd PC

(57) ABSTRACT

A method for optimizing a shape of a replacement valve leaflet, wherein the shape of the replacement valve leaflet is determined by defining variable parameters of the replacement valve leaflet. The variable parameters may comprise: a valve height; a leaflet coaptation height, a first set of two control points for a first B-spline plane of symmetry; and a second set of two control points for a second B-spline plane tangent to a frame of the valve. The method may further comprise creating iterations of potential shapes of the replacement valve leaflet by changing one or more of the variable parameters using modeling software. The method may also comprise calculating the maximum stresses or strains on each of the potential shapes.

23 Claims, 18 Drawing Sheets

(56) References Cited

U.S. PATENT DOCUMENTS

| | | | |
|---|---|---|---|
| 9,779,496 B2 | 10/2017 | Jackson et al. | |
| 9,827,089 B2 | 11/2017 | Bruchman et al. | |
| 10,039,638 B2 | 8/2018 | Bruchman et al. | |
| 2014/0155995 A1* | 6/2014 | Sun | A61F 2/2412 623/2.18 |
| 2014/0172079 A1 | 6/2014 | Bruchman et al. | |
| 2016/0035087 A1 | 2/2016 | Jackson et al. | |
| 2016/0067038 A1 | 3/2016 | Park et al. | |
| 2017/0156854 A1* | 6/2017 | Hammer | A61F 2/2412 |
| 2017/0365057 A1 | 12/2017 | Jackson et al. | |
| 2019/0095589 A1* | 3/2019 | Kim | G16H 30/40 |
| 2019/0240025 A1* | 8/2019 | Silberbach | A61L 27/16 |
| 2021/0205099 A1* | 7/2021 | Parr | A61F 5/10 |

OTHER PUBLICATIONS

Li et al., "Simulated Transcatheter Aortic Valve Deformation: a Parametric Study on the Impact of Leaflet Geometry on Valve Peak Stress", "Int. J. Numer. Meth. Biomed. Engng.", Jul. 26, 2016, pp. 14, vol. 2017, Publisher: Wiley Online Library (wileyonlinelibrary.com).

Xu et al., "A Framework for Designing Patient-Specific Bioprosthetic Heart Valves Using Immersogeometric Fluid-Structure Interaction Analysis", "Int. J. Numer. Mech. Biomed. Engng", Oct. 22, 2017, pp. 25, vol. 2018, No. 34, Publisher: Wiley (wileyonlinelibrary.com).

Abbasi et al., "A Geometry Optimization Framework for Transcatheter Heart Valve Leaflet Design", "Journal of the Mechanical Behavior of Biomedical Materials", 2020, pp. 9, vol. 2020, No. 102, Publisher: Elsevier.

* cited by examiner

LEAFLET FREE-EDGE (TOP VIEW)

LEAFLET FREE-EDGE (SIDE VIEW)

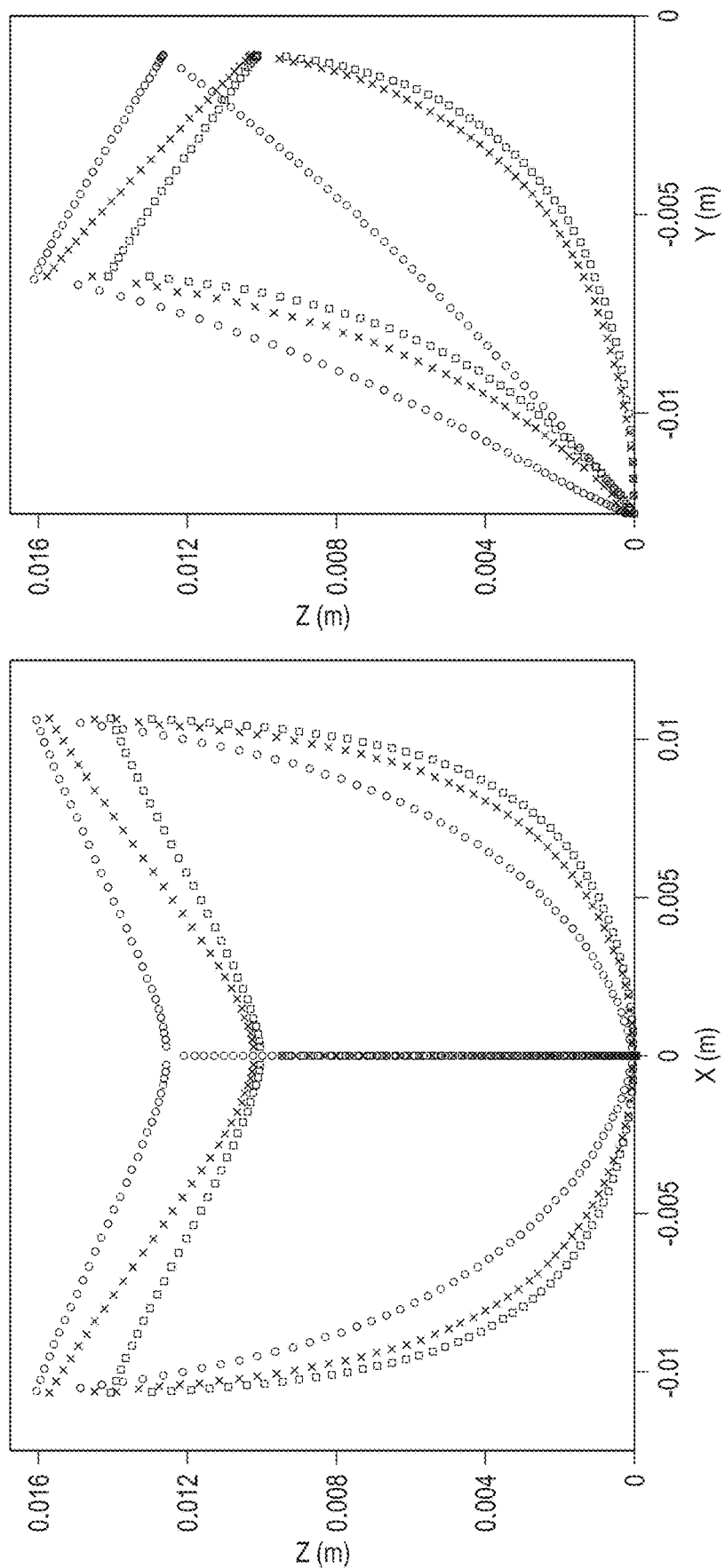

OPTIMIZATION OF REPLACEMENT HEART VALVE LEAFLETS

PRIORITY

This application claims priority to U.S. Provisional Application No. 62/776,170, filed Dec. 6, 2018 and entitled OPTIMIZATION OF REPLACEMENT HEART VALVE LEAFLETS, the disclosure of which is incorporated herein by reference in its entirety.

FIELD OF THE DISCLOSURE

The present disclosure relates generally to valve leaflet design optimization. In particular, but not by way of limitation, the present disclosure relates to systems, methods and apparatuses for designing optimized valve leaflets for replacement heart valves.

BACKGROUND

Heart valve replacement (via both surgical and minimally invasive procedures) is an established treatment for patients with heart diseases affecting the valves, including, for example, aortic stenosis. It is known and recognized that leaflet geometry has a key role in structural and hemodynamic performance of bioprosthetic heart valves. Excessive mechanical stress and/or strain on the leaflets leads to accelerated tissue degeneration and diminished long-term valve durability. Therefore, a need exists to design leaflets in ways that reduce mechanical stress and/or strain.

BRIEF DESCRIPTION OF THE DRAWINGS

FIG. 6B is a schematic plot of the fixed-boundary edge, free-edge, and symmetric curves for the best leaflet designs with respect to the lower and upper optimization boundaries for a 26-mm replacement valve.

SUMMARY

Figure 1A:
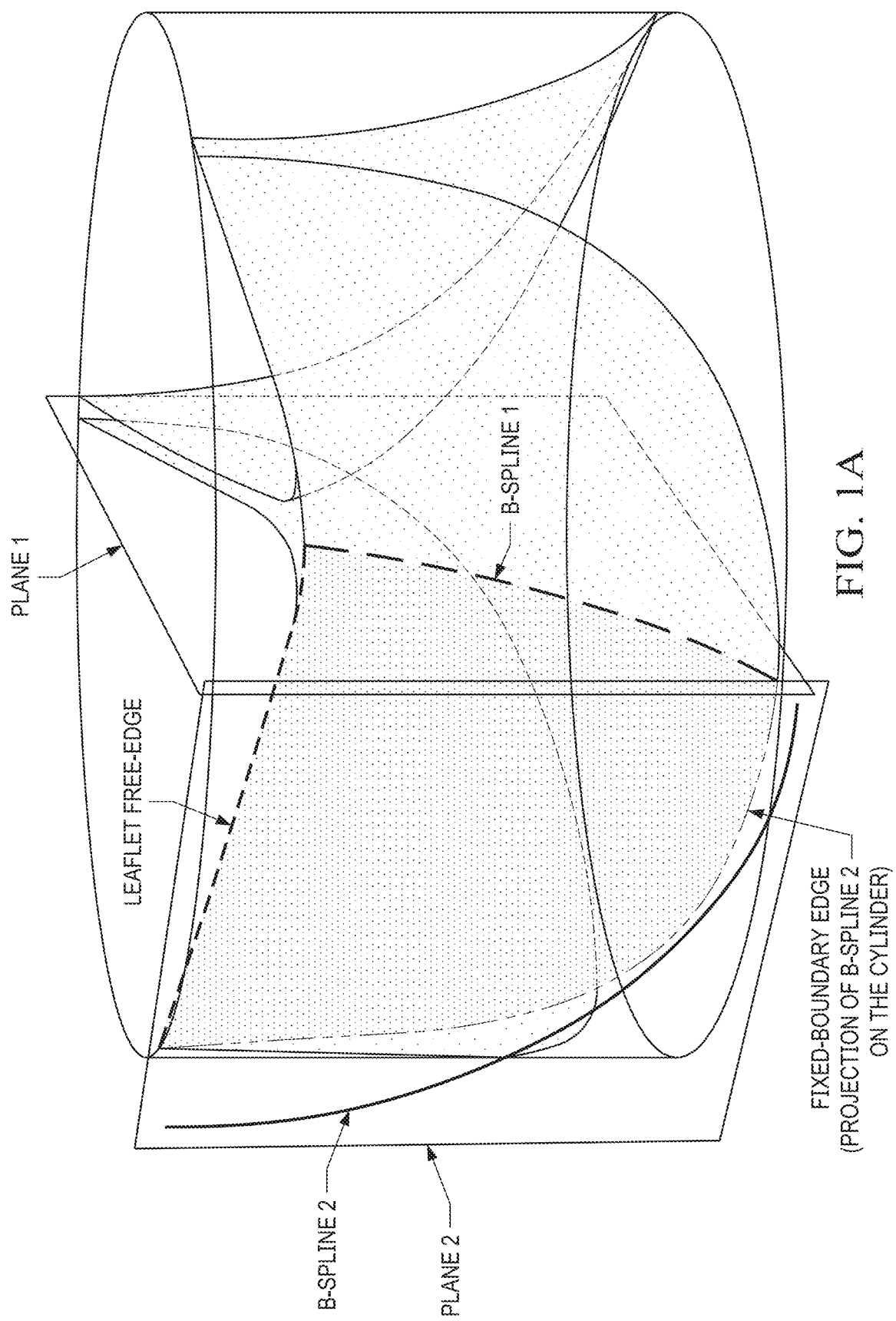
FIG. 1A shows design variables in parameterization on a model of a geometry of a valve leaflet.

An aspect of the present disclosure provides a method for creating an optimized shape for a replacement valve leaflet. The method may comprise defining variable parameters of the replacement valve leaflet. The variable parameters may comprise: a valve height; a leaflet coaptation height, a first set of two control points for a first B-spline plane of symmetry; and a second set of two control points for a second B-spline plane tangent to a frame of the valve. The method may further comprise creating iterations of potential shapes of the replacement valve leaflet by changing one or more of the variable parameters using modeling software. The method may also comprise calculating the maximum stresses or strains on each of the potential shapes.

Yet another aspect of the disclosure provides a replacement valve leaflet, wherein the shape of the replacement vale leaflet is determined by defining variable parameters of the replacement valve leaflet. The variable parameters may comprise: a valve height; a leaflet coaptation height, a first set of two control points for a first B-spline plane of symmetry; and a second set of two control points for a second B-spline plane tangent to a frame of the valve. The method may further comprise creating iterations of potential shapes of the replacement valve leaflet by changing one or more of the variable parameters using modeling software. The method may also comprise calculating the maximum stresses or strains on each of the potential shapes.

Yet another aspect provides a non-transitory, tangible computer readable storage medium, encoded with processor readable instructions to perform a method for creating an optimized shape for a replacement valve leaflet. The method may comprise defining variable parameters of the replacement valve leaflet. The variable parameters may comprise: a valve height; a leaflet coaptation height, a first set of two control points for a first B-spline plane of symmetry; and a second set of two control points for a second B-spline plane tangent to a frame of the valve. The method may further comprise creating iterations of potential shapes of the replacement valve leaflet by changing one or more of the variable parameters using modeling software. The method may also comprise calculating the maximum stresses or strains on each of the potential shapes.

DETAILED DESCRIPTION

The word "exemplary" is used herein to mean "serving as an example, instance, or illustration." Any embodiment described herein as "exemplary" is not necessarily to be construed as preferred or advantageous over other embodiments.

An aspect of the present disclosure provides an automatic optimization framework for reducing maximum stress value of replacement heart valve leaflets. Although specific aspects of the disclosure refer to experiments and models conducted in view of a particular kind of heart valve—namely, bioprosthetic aortic valves of the type implanted via minimally-invasive transcatheter procedures—the optimization framework may also be used to optimize other types of heart replacement valves. These heart replacement valves may include those for valves other than aortic valves, ones that are manufactured from polymeric materials rather than bioprosthetic (i.e., animal tissue) materials, and ones that are implanted via an invasive surgical procedure. In embodiments, the optimization frameworks of the present disclosure may be implemented through commercially available software programs.

Transcatheter aortic valve replacement (TAVR) is an established therapy alternative to surgical valve replacement in high-risk and intermediate-risk patients with severe aortic stenosis. The use of this treatment has become increasingly common worldwide since 2002, and to date, more than 350,000 patients have undergone TAVR across the globe. Although TAVR is an alternative and less-invasive treatment for high-risk and intermediate-risk patients, surgical aortic valve replacement (SAVR) is still considered the gold standard treatment option for low-risk patients with severe aortic stenosis. Currently, there are structural differences between the types of valves used in SAVR and the type used in TAVR. SAVR devices can be either mechanical or bioprosthetic, and can be constructed with properties that give them rigidity and durability because they are inserted via open-heart surgery. For example, they may have more flexible frames or thicker valve leaflets. TAVR devices, by necessity, must be able to fit within a catheter and implanted within an opening created by a stent, and therefore may have properties (such as rigidity) that make them more prone to degradation over time. Further, TAV leaflets may be subject to greater stress if there are difficulties with the stent, such as incomplete or eccentric TAV stent expansion or stent crimping.

TAVR is approved for intermediate-risk, high-risk, and inoperable patients with aortic stenosis. It has also been recently approved for low-risk patients as well, even though long-term durability is still not known. However, because TAVR is far less invasive than open-heart surgery, with an average recovery time of three to five days, more and more low surgical risk patients are requesting TAVR.

To expand the TAVR indications effectively to low-risk younger patients, transcatheter aortic valve (TAV) long-term durability should match with that of surgical bioprostheses. The rate of structural valve degeneration in surgical bioprostheses is known to be less than 15% at 10 years. However, in comparison to the amount of data available about the durability of surgical aortic valves (SAVs), there is limited clinical data on the long-term durability of TAV devices; most of the available clinical trial data are on patients 80 years or older. Studies have estimated that the structural valve degeneration rate of commercially available TAV replacement heart valves under the brand and model names Cribier-Edwards, Edwards SAPIEN, and Edwards SAPIEN XT was approximately 50% at eight years. This rate of degeneration is not ideal for low-risk, younger patients whose life expectancies may be well beyond eight years. Therefore, proper evaluation of the long-term durability of TAVs and other heart valves is essential for potential expansion of this treatment to lower-risk younger patients.

Durability of tissue heart valves results primarily from their ability to resist two distinct yet potentially synergistic failure mechanisms: 1) calcification of the tissue and 2) fatigue-induced structural deterioration of the tissue. Since most of the TAV devices are fabricated from chemically treated bovine or porcine pericardium tissue (such devices being referred to herein as "bioprosthetic"), it can be postulated that the structural deterioration of TAVs occurs via the two failure mechanisms. It has been shown that mechanical stress on bioprosthetic heart valve leaflets can be linked with the leaflet degeneration. Though the term "stress" is often used alone throughout the disclosure, in many cases, the "strain" on tissue is also an appropriate measurement of deforming forces. It is known in the art that "stress" is a measurement of a deforming force per unit area of an object (in this case, heart valve tissue or materials) and "strain" is a measurement of relative change in length caused by a deforming force. In the present disclosure, when discussing measurement of forces, "stress" may sometimes be construed to mean "stress and/or strain."

There is a correlation between the regions of tissue rupture in bioprosthetic heart valves and excessive mechanical stress on the leaflets. Moreover, it is widely accepted that high stress regions initiate calcification by damaging the structural integrity of tissue. Therefore, proper evaluation of the leaflet stress distribution is essential to assess long-term durability of TAV devices. Minimizing the peak stress value in bioprosthetic heart valve leaflets is a crucial to maximize long-term durability of the tissue heart valves. Therefore, parametric studies on the effect of leaflet geometry on valve peak stress have been inspired and developed.

The experiments described in the present disclosure were aimed at developing an automatic optimization framework (i.e., a method) using commercially available software packages to assess the impact of TAV leaflet design on the maximum stress value of the leaflets under dynamic physiological loading conditions. Optimized leaflet designs were achieved through use of the method of the present disclosure for two different commonly-used TAV sizes: 23 mm and 26 mm. In the present disclosure, the term "optimized" may be construed to mean "achieved a reduction in stress and/or strain levels." Subsequently, the stress levels optimized leaflet designs were compared with stress levels of the designs of two commercially available bioprostheses: (i) a Carpentier-Edwards PERIMOUNT Magna surgical bioprosthesis and (ii) an Edwards SAPIEN 3 transcatheter heart valve. Both of these bioprostheses are considered as gold-standard devices in today's practice of heart valve replacement.

To demonstrate the efficacy of the optimization framework of the present disclosure, the design of TAV leaflets was parameterized by two second-order non-uniform rational B-splines (NURBS) curves and particle swarm optimization method was used to examine the optimization design space. Though the study discussed throughout the present disclosure pertains to measurements and calculations specific to TAV valves, other similar valves with different measurements and calculations may be designed using the optimization framework. Here, optimized leaflet geometries for both 23-mm and 26-mm TAVs were obtained under dynamic physiological loading conditions. Leaflet stress distributions of the optimized TAV leaflet geometries were compared with those of two commercially available bioprostheses (i) Carpentier-Edwards PERIMOUNT Magna surgical bioprosthesis and (ii) Edwards SAPIEN 3 transcatheter heart valve. A considerable reduction in the maximum in-plane principal stress was observed in the optimized TAV geometries compared to the commercially available bioprostheses. The optimization results underline the opportunity to improve leaflet design in the next generation of TAVs to potentially increase long-term valve durability. The method of the present disclosure for obtaining these optimized designs may be used to manufacture new replacement valve leaflets, whether for aortic or non-aortic valves, out of bioprosthetic or other materials such as polymers. It is contemplated that replacement valve leaflets for surgical replacement valves may also use the optimization method and resulting leaflet designs of the present disclosure.

An aspect of the disclosure pertains to parameterization and optimization of the TAV leaflet geometry. An automated geometry optimization framework was developed to reduce TAV leaflet stress under physiological loading condition. TAV leaflets with uniform thickness (t) were considered to be attached to a frame with a uniform thickness of 0.5 mm and an external diameter of D. Two different external diameters (D) were considered in this study: (i) 23 mm and (ii) 26 mm. Design variables were defined using two second-order Non-uniform rational B-splines (NURB S) curves.

Figure 1B:
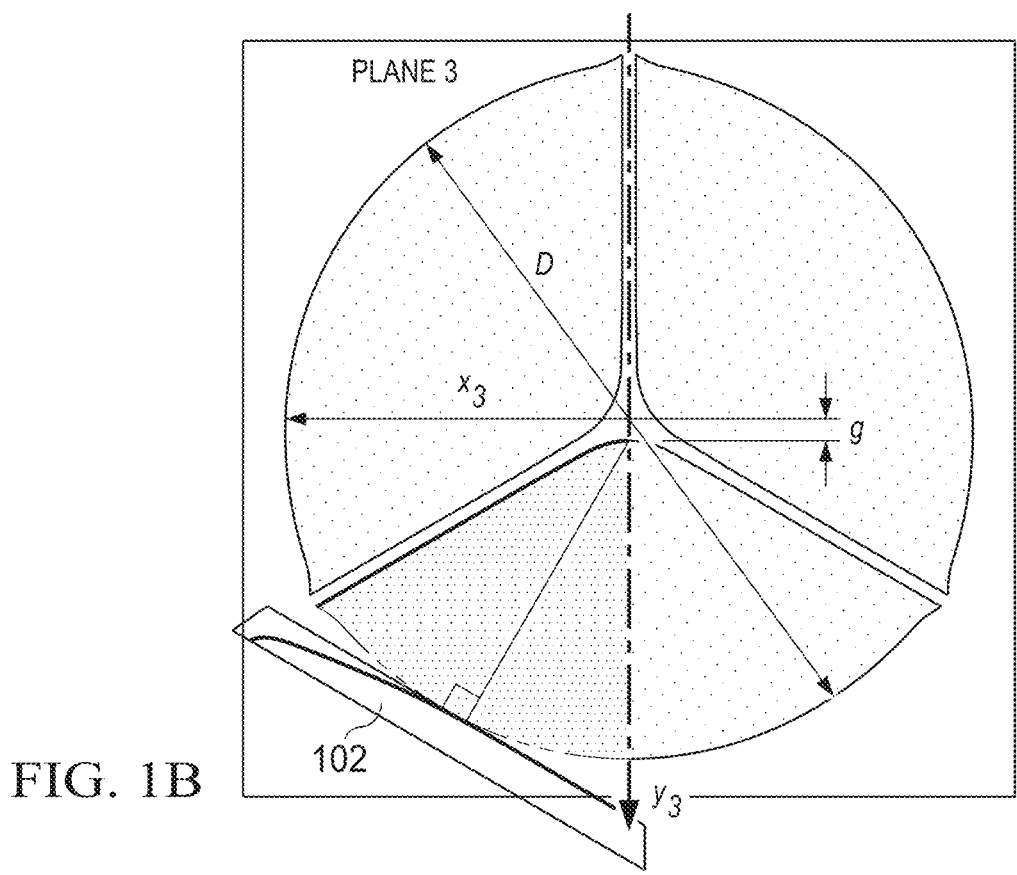
FIG. 1B shows a top view of certain design variables of FIG. 1A.
Figure 1C:
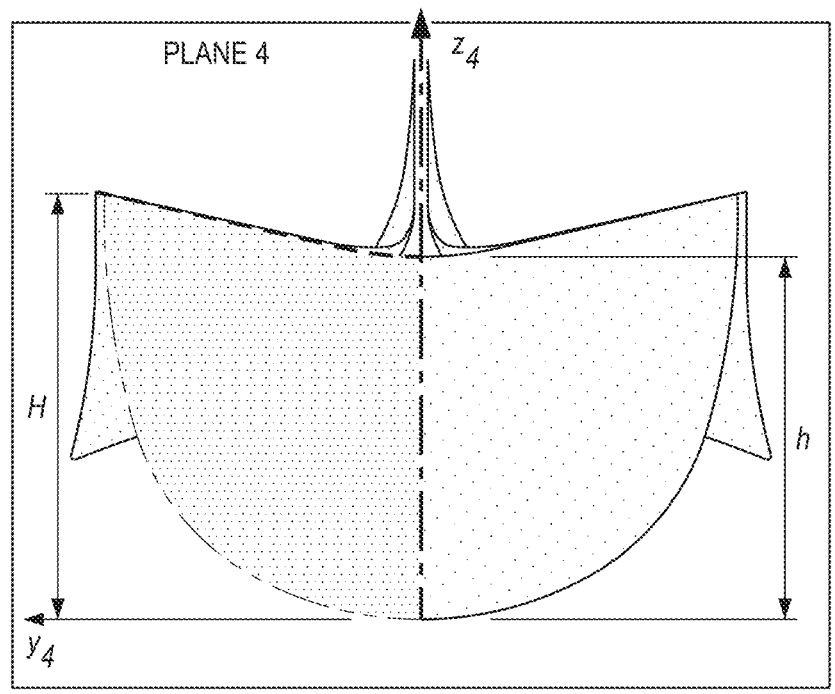
FIG. 1C shows a side view of certain design variables of FIG. 1A.
Figure 1D:
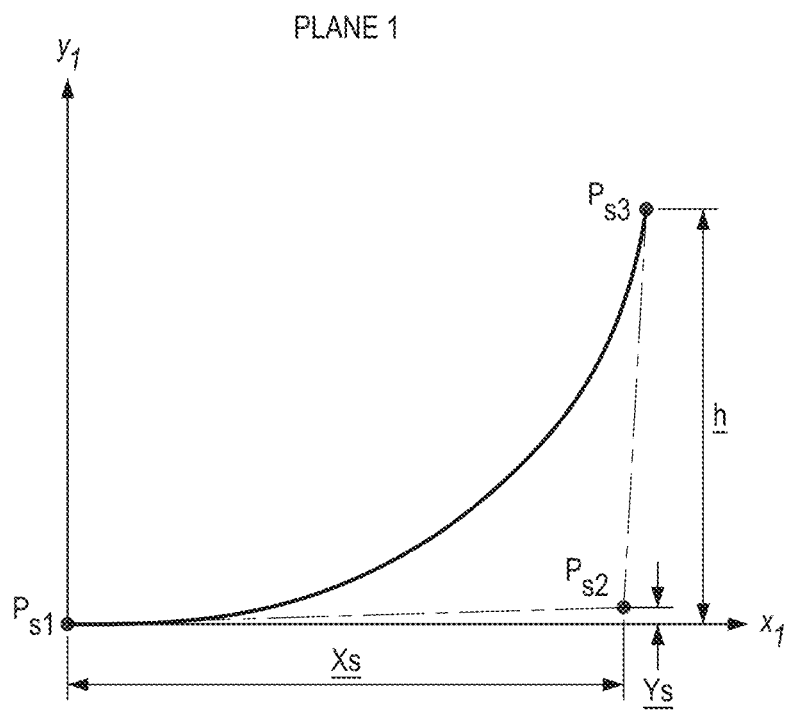
FIG. 1D shows control points of B-spline plane 1 of FIG. 1A.
Figure 1E:
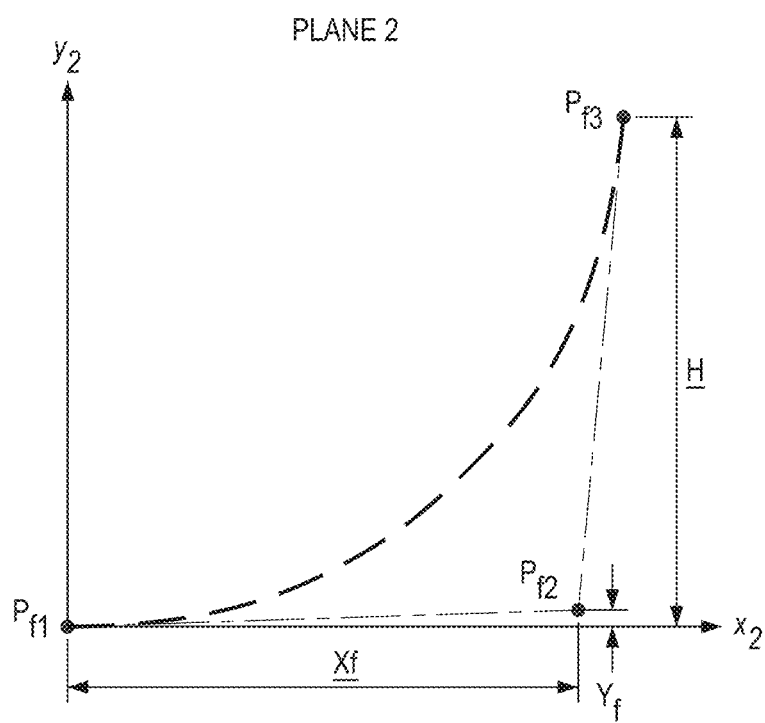
FIG. 1E shows control points of B-spline plane 2 of FIG. 1A.

FIGS. 1A, 1B, 1C, 1D, 1E illustrate six parameters used in the experiments of this disclosure to explore and model all possible geometrical configurations of TAV leaflets. As shown, leaflets have an unusual geometric shape, and many possible parameters of the shape could be used to try to alter the shape. The approach of the present disclosure, however, provides an effective and reliable method to explore all possible geometrical configurations for the TAVs with only 6 parameters. The use of six parameters allows for effective, yet thorough modeling through available software. The six variables used were valve height (H), leaflet coaptation height (h) (i.e., a height at which one or more of the leaflets meets with one or more other leaflets of the valve), (both shown in FIG. 1C), and two control points for each one of the two second-order B-splines. The B-spline planes are best depicted in FIG. 1. The two control points for each of the B-spline planes (i.e., $X_s$ and $Y_s$ for B-spline 1 in the plane of symmetry (Plane 1), and $X_f$ and $Y_f$ for B-spline 2 in Plane 2 which is tangent to the TAV frame, as shown in FIG. 1A.), are shown in FIG. 1D. In the parameterization procedure, B-spline plane 2 (102) was subsequently projected on the cylinder, which represents the TAV frame, to create a fixed-boundary edge for the leaflet. This projection of the plane 102 is best seen from the top view in FIG. 1B. The B-splines' control points determine the shape of the fixed-boundary edge (seen in FIG. 1D) and the symmetric curve (seen in FIG. 1E). After projecting the B-spline plane 2 (102) onto the cylinder, the leaflet free-edge that connects the commissure to the point of leaflet coaptation was reconstructed automatically based on the fixed-boundary edge and the symmetric curve. In implementation, valve leaflets for replacement valves typically have a small gap where the leaflets meet because of their unique shape; therefore, a small gap (g) with a constant value of 0.6 mm was considered at the center of the leaflets at the load-free initial configuration, which is best seen in FIG. 1B. During operation of a valve (either in experiments or in actual use), the leaflets separate and meet repeatedly to allow blood to flow in one direction through the valve when open and prevent backflow when closed, and the experiments herein contemplate measurements being taken when there is a "load" on the leaflet valves (i.e., after valve replacement/implantation) and when they are "load free" (i.e., prior to valve replacement/implantation).

Figure 1F:
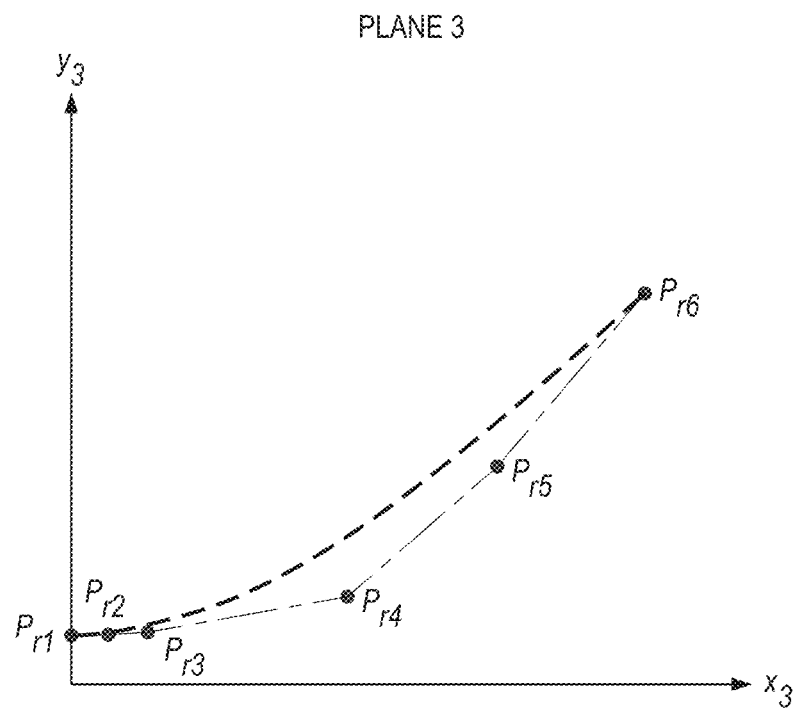
FIG. 1F shows control points of B-spline plane 3 of FIG. 1B.
Figure 1G:
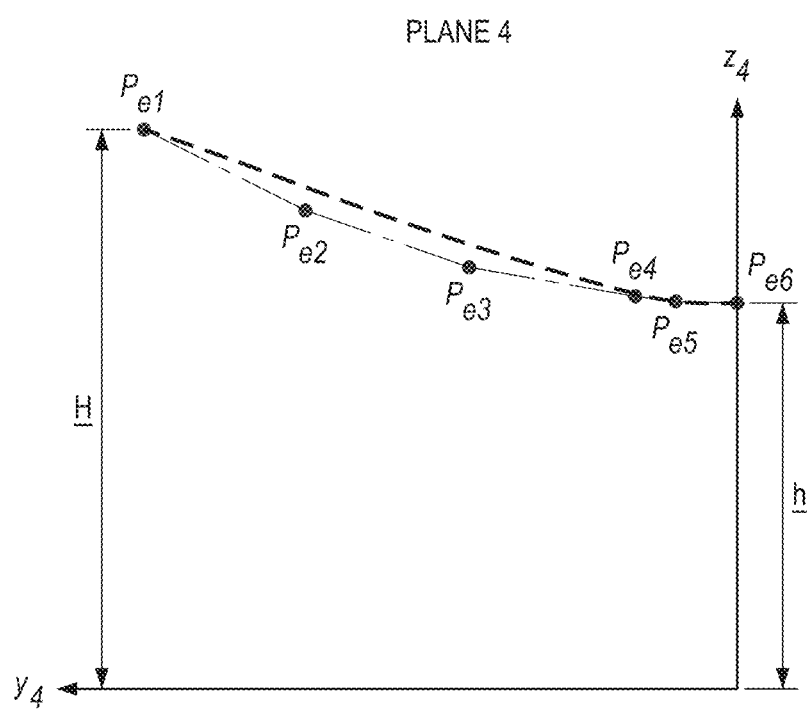
FIG. 1G shows control points of B-spline plane 4 of FIG. 1C.

FIGS. 1F and 1G show the control points for the B-spline planes 3 and 4 of FIGS. 1B and 1C, respectively. As shown in FIGS. 1B and 1C, the leaflet free-edge that connects the commissure to the point of leaflet coaptation was reconstructed based on projection of two B-splines with degree of 5 defined in Plane 3, the top plane of the TAV, and Plane 4, passing through TAV centerline and perpendicular to the plane of symmetry (Plane 1). FIG. 1F illustrates five control points, i.e., $P_{r1}(x_{r1}, y_{r1})$, $P_{r2}(x_{r2}, y_{r2})$, $P_{r3}(x_{r3}, y_{r3})$, $P_{r4}(x_{r4}, y_{r4})$, $P_{r5}(x_{r5}, y_{r5})$, and $P_{r6}(x_{r6}, y_{r6})$, determine the shape of B-spline in Plane 3. In addition, FIG. 1G shows another five control points, i.e., $P_{e1}(x_{e1}, y_{e1})$, $P_{e2}(x_{e2}, y_{e2})$, $P_{e3}(x_{e3}, y_{e3})$, $P_{e4}(x_{e4}, y_{e4})$, $P_{e5}(x_{e5}, y_{e5})$, and $P_{e6}(x_{e6}, y_{e6})$, which determine the shape of B-spline in Plane 4.

In the present study, non-uniform rational B-splines (NURBS) curves were used to create transcatheter aortic valve (TAV) leaflet geometry. A NURBS curve is defined by $$C(t) = \frac{\sum_{i=0}^{n} N_{i,p}(t) w_i P_i}{\sum_{i=0}^{n} N_{i,p}(t) w_i}$$

where p is the order of a NURBS curve, $N_{i,p}$ are the B-spline basis functions, $P_i$ are control points, n is the number of control points and $w_i > 0$ is a weighting factor. B-spline basis functions given by $$N_{i,0}(t) = \begin{cases} 1 & \text{if } t_i \le t_{i+1} \text{ and } t_i < t_{i+1} \\ 0 & \text{otherwise} \end{cases}$$

$$N_{i,j}(t) = \frac{t - t_i}{t_{i+j} - t_i} N_{i,j-1}(t) + \frac{t_{i+j+1} - t}{t_{i+j+1} - t_{i+1}} N_{i+1,j-1}(t)$$

where $t_i$ are the knots forming a knot vector. The knot vector T is a set of m+1 non-decreasing numbers.

$$T = \{t_0, t_1, \ldots, t_m\}$$

Also, the degree of the basis functions p can be defined as $$p = m - n - 1$$

In this study, TAV leaflets with uniform thickness (t) were considered to be attached to a frame with a uniform thickness of 0.5 mm and an external diameter of D. The 3D leaflet geometry comprises of two NURBS curves (i) the symmetric curve and (ii) the fixed-boundary edge. The leaflet free-edge, that connects the commissure to the point of leaflet coaptation, was subsequently reconstructed based on the symmetric curve and the fixed-boundary edge. The symmetric curve was generated using a second order NURBS curve (B-spline 1) in the plane of symmetry. The three controlling points of the B-spline, Ps1(xs1, ys1), Ps2(xs2, ys2) and Ps3(xs3, ys3), are shown in FIG. S2. xs2 and ys2 were considered as the two design parameters for B-spline 1 in the plane of symmetry, Xs and Ys, respectively. In addition, ys3 was taken as a parameter of h (leaflet coaptation height) to change coaptation height of the leaflets. As a result, the shape of the belly region was controlled by three parameters, i.e., Xs, Ys and h.

B-spline 2 controls the shape of the fixed-boundary edge. To create a fixed-boundary edge for the leaflet, B-spline 2 was projected on the cylinder (the TAV frame) in the MATLAB code. The three controlling points of B-spline 2, Pf1(xf1, yf1), Pf2(xf2, yf2) and, Pf3(xf3, yf3) are shown in FIG. S2. xf2 and yf2 were considered as the two design parameters for B-spline 2, Xf and Yf, respectively. In addition, yf3 was taken as a parameter of H (valve height) to change the TAV height. As a result, the shape of the fixed-boundary edge was controlled by three parameters, i.e., Xf, Yf and H.

The mathematical formulation and further details of the parameterization in MATLAB® (a multi-paradigm numerical programming language developed by The MathWorks, Inc. of Natick, Mass., USA) are shown in the table below. The coding shown and described herein is exemplary only, and the resulting methods may be implemented in other software code without departing from the scope of the present disclosure.

TABLE A

The coordinates of control points with respect to the local coordinate systems defining the fixed-boundary edge, the symmetric curve, and the leaflet free-edge.

| Control Points | First coordinate | Second coordinate |
| --- | --- | --- |
| $P_{s1}$ | 0 | 0 |
| $P_{s2}$ | $X_s$ | $Y_s$ |
| $P_{s3}$ | $\dfrac{D}{2} - \dfrac{t}{2\cos(\frac{\pi}{6})} - g$ | h |
| $P_{f1}$ | 0 | 0 |
| $P_{f2}$ | $X_f$ | $Y_f$ |
| $P_{f3}$ | $D\tan(\frac{\pi}{6}) - \dfrac{t}{2\cos(\frac{\pi}{6})}$ | H |
| $P_{r1}$ | 0 | $\left(\dfrac{t}{2\cos(\frac{\pi}{6})} + g\right)$ |
| $P_{r2}$ | $0.085 \times \dfrac{D}{2}\cos(\tilde{\alpha})$ | $0.9509 \times \left(\dfrac{t}{2\cos(\frac{\pi}{6})} + g\right)$ |
| $P_{r3}$ | $0.2126 \times \dfrac{D}{2}\cos(\tilde{\alpha})$ | $1.268 \times \left(\dfrac{t}{2\cos(\frac{\pi}{6})} + g\right)$ |
| $P_{r4}$ | $0.59 \times \dfrac{D}{2}\cos(\tilde{\alpha})$ | $0.205 \times \dfrac{t}{2\cos(\frac{\pi}{6})} - 0.59 \times \dfrac{D}{2}\sin(\tilde{\alpha})$ |
| $P_{r5}$ | $0.8 \times \dfrac{D}{2}\cos(\tilde{\alpha})$ | $\dfrac{t}{10\cos(\frac{\pi}{6})} - 0.8 \times \dfrac{D}{2}\sin(\tilde{\alpha})$ |
| $P_{r6}$ | $\dfrac{D}{2}\cos(\tilde{\alpha})$ | $\dfrac{D}{2}\sin(\tilde{\alpha})$ |
| $P_{e1}$ | $\dfrac{D}{2}\cos(\tilde{\alpha})$ | H |
| $P_{e2}$ | $0.8 \times \dfrac{D}{2}\cos(\tilde{\alpha})$ | $0.8 \times H + 0.2 \times h$ |
| $P_{e3}$ | $0.59 \times \dfrac{D}{2}\cos(\tilde{\alpha})$ | $0.59 \times H + 0.41 \times h$ |
| $P_{e4}$ | $0.2126 \times \dfrac{D}{2}\cos(\tilde{\alpha})$ | $1.0095 \times h$ |

TABLE A-continued

The coordinates of control points with respect to the local coordinate systems defining the fixed-boundary edge, the symmetric curve, and the leaflet free-edge.

| Control Points | First coordinate | Second coordinate |
| --- | --- | --- |
| $P_{e5}$ | $0.085 \times \dfrac{D}{2} \cos(\tilde{\alpha})$ | $1.0017 \times h$ |
| $P_{e6}$ | 0 | h |

$\tilde{t}$ is leaflet thickness;
g is a gap at the center of the leaflets at the load-free initial configuration (0.6 mm), and
$\tilde{\alpha} = at(D - 2\tilde{t}/D\sqrt{3})$.

Figure 2:
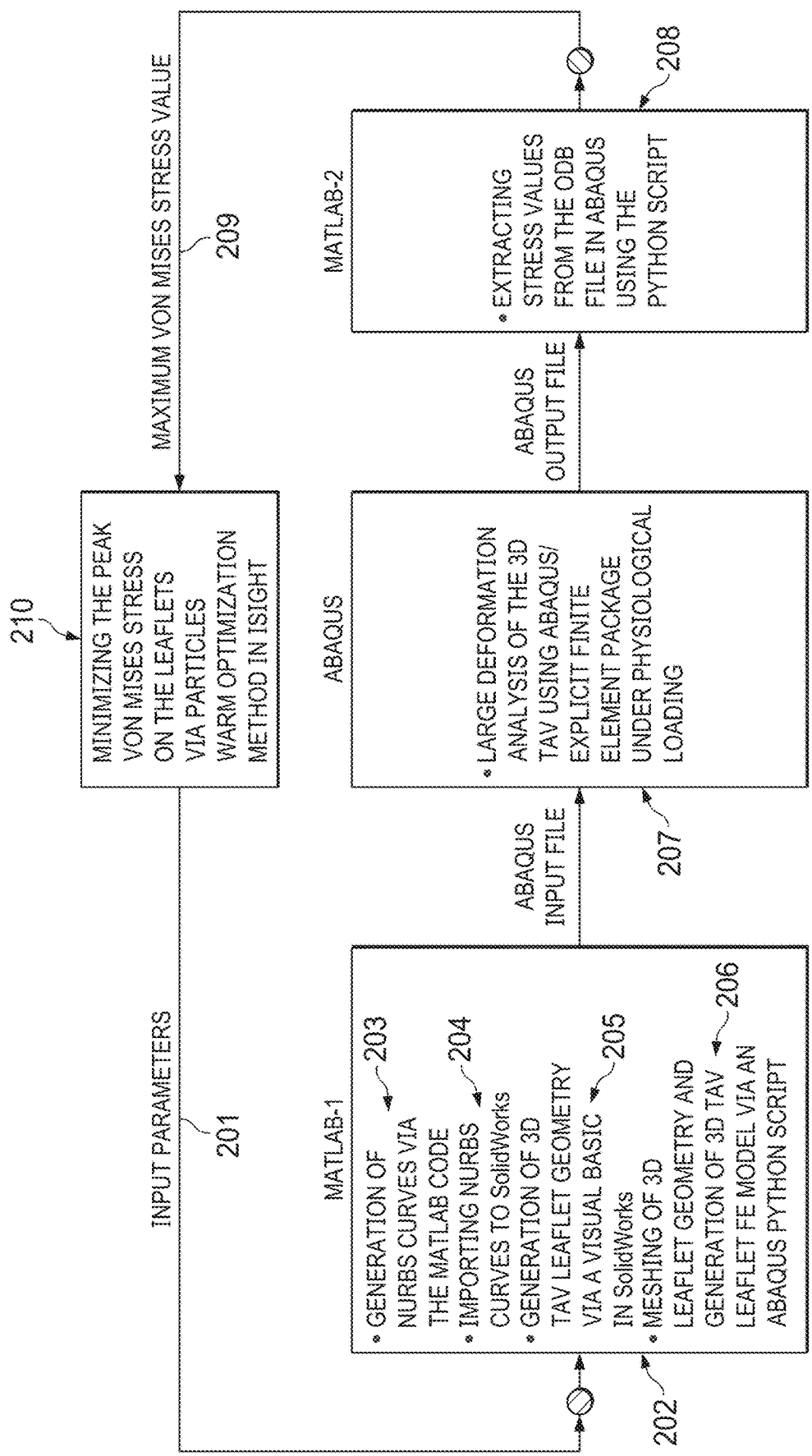
FIG. 2 is a flowchart for an optimization framework of the valve leaflet geometry.

The flowchart shown in FIG. 2 shows an overview of how the optimization procedure was implemented in the experimental study described in the present disclosure. The input parameters 201 (i.e., those shown in the preceding paragraphs and in Table A) were input into the first steps of the overall optimization procedure 202. Using an ABAQUS® Python script (computer engineering software for finite element analysis developed by Dassault Systémes, SE, of Vélizy-Villacoublay, France), NURBS curves were generated in MATLAB at step 203. Then the NURBS curves were imported into SolidWorks (a CAD drawing and modeling software program developed by Dassault Systemes) at step 204.

Figure 3:
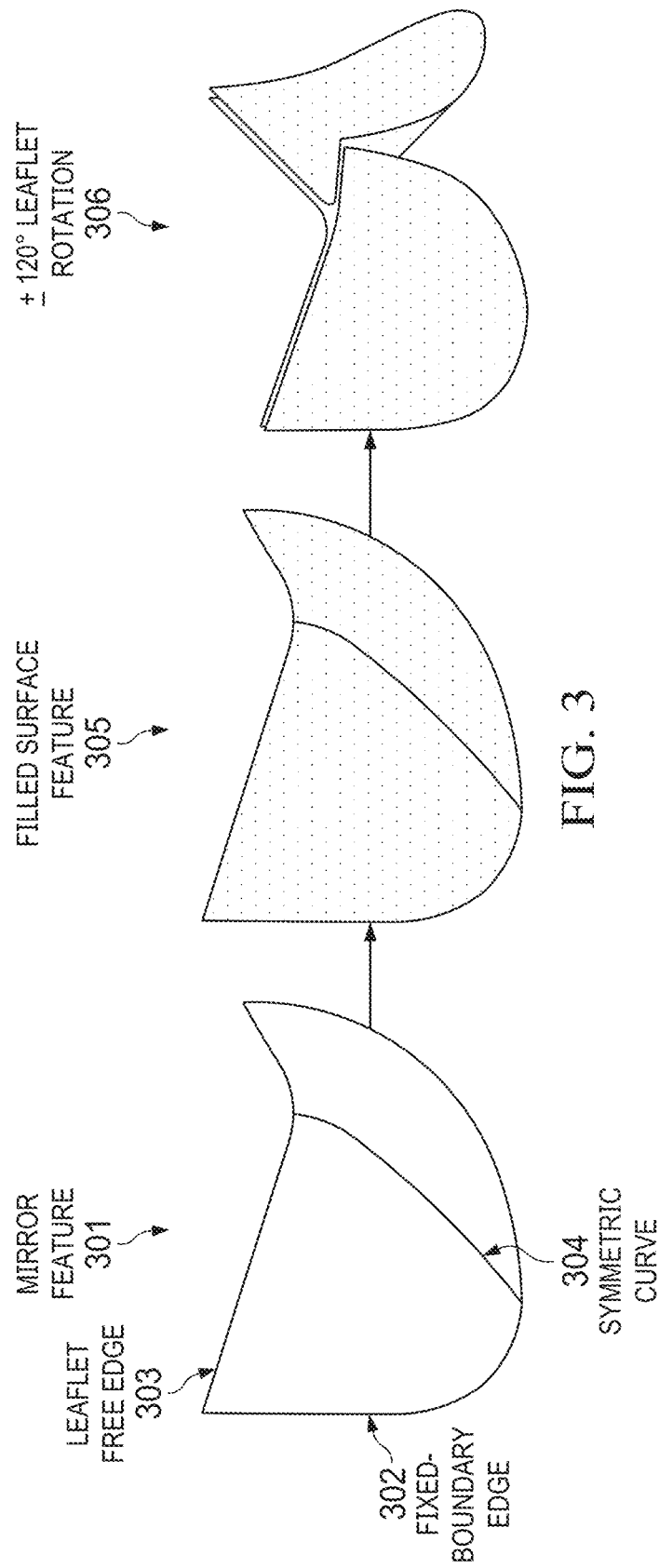
FIG. 3 shows a reconstruction of the leaflet geometry in an engineering software program.

Turning briefly to FIG. 3, shown is the generation of a model 301 of the valve leaflets in SolidWorks® Due to the symmetry of the TAV leaflet design, the fixed-boundary edge 302 and the leaflet free-edge 303 were mirrored with respect to the plane of symmetry (plane 1 (304)). Then, a surface 305 was created based on the boundary curves of the leaflet using Filled Surface command in SolidWorks. The symmetric curve was used as a constraint curve in the procedure. Subsequently, the constructed leaflet was rotated ±120° about the center of the TAV frame to create the other two leaflets as shown in the figure of the rotated leaflet 306.

Figure 4:
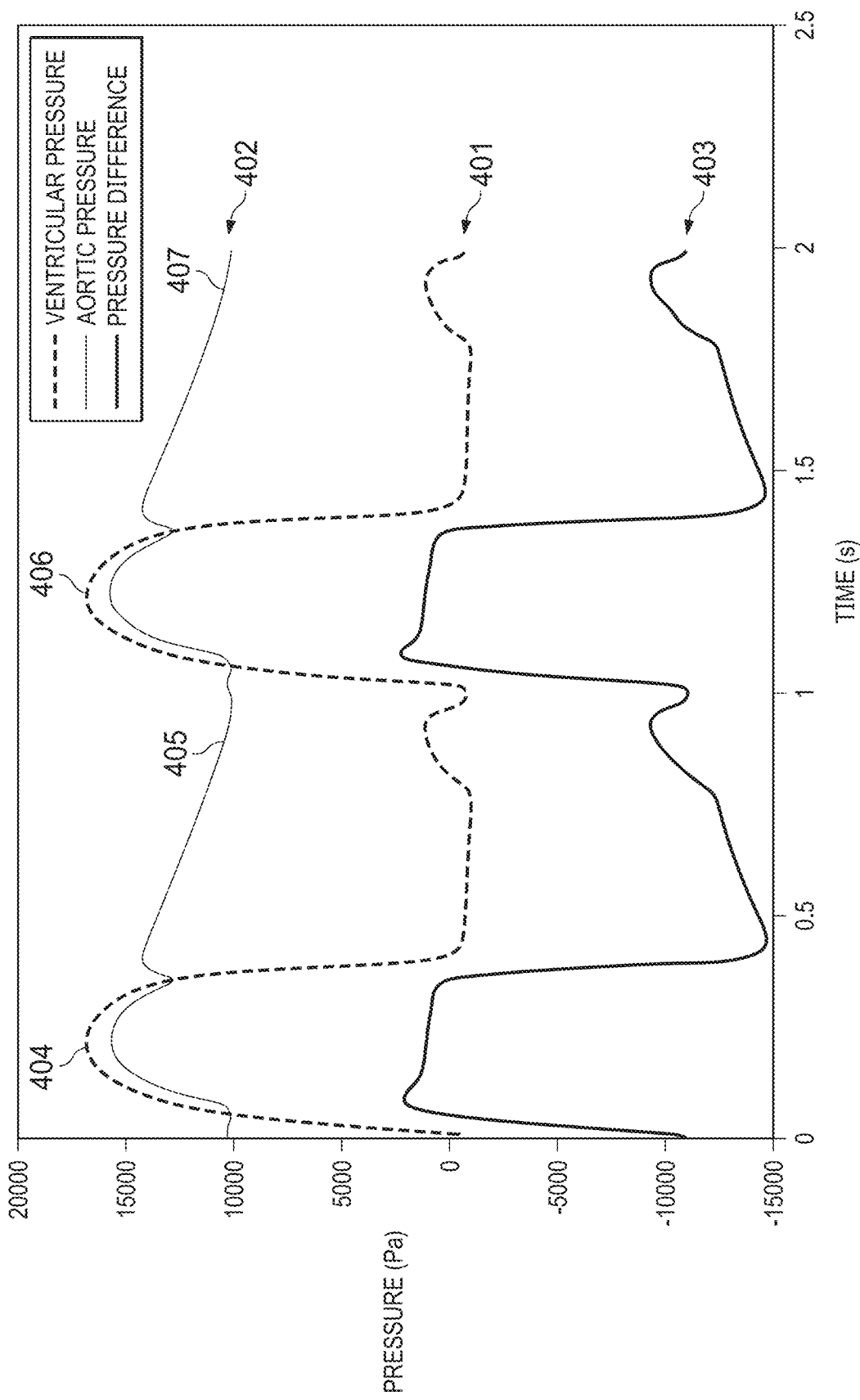
FIG. 4 shows results from a test of an aortic valve, showing a variation in pressure in the left ventricle (dashed line) and the aorta (solid line), wherein the wave pressure (dash-dot line) may be defined as the pressure difference between the left ventricle and the aorta.

Then using an ABAQUS Python script, the valve geometry was imported to ABAQ, US and discretized using S4 and S3 shell elements. In the Python script, the average size of mesh in finite element (FE) simulations was set to be 0.3 mm, as shown in step 206. Due to high radial strength of TAV frames that is needed to provide positional stability of the valves, the stent frame was considered to be rigid. As a result, all nodes along the fixed-edge curve were considered to be fixed in the FE simulations. In addition, a uniform leaflet thickness of 0.5 mm was considered in the simulations. Then, as described in step 207 in FIG. 2, a physiological transvalvular pressure gradient meant to simulate the ventricular and aortic pressure on a replacement aortic valve was applied to the leaflets as a loading condition. Turning briefly to FIG. 4, the pressure, as measured in Pa, is graphed showing each of ventricle pressure 401, aortic pressure 402, and the difference between the two over two seconds of time 403. The two peaks 404, 406 and troughs 405, 407 in applied pressure were meant to simulate pressure curves during two cardiac cycles.

In the optimization process, calculations regarding material properties were made in order to accurately model the predicted effects of pressure on the material. In the present experiments, the TAV leaflets were considered to be isotropic nonlinear hyperplastic material. A fourth-order reduced polynomial strain-energy function was fitted to experimental raw data obtained from biaxial testing of bovine pericardium samples, which is shown in Table 1. The strain-energy function determines relationship between stress and strain.

TABLE 1

Coefficients of the fourth-order reduced polynomial strain-energy function.

| C10 | C20 | C30 | C40 |
| --- | --- | --- | --- |
| 1.56941E+5 | 8.59024E+5 | −6.50847E+5 | 5.59565E+6 |

$$W = \Sigma_{i=1}^{4} C_{i0}(I_1 - 3)^i$$

Here, $C_{i0}$ are constants and $I_1$ is the first principal invariant of the left Cauchy-Green deformation tensor. The coefficients of fourth-order polynomial strain-energy function were shown in Table 1. In the dynamic FE analysis, density of the leaflets was considered to be 1,100 kg/m3, and a Rayleigh damping coefficient α with a constant value of 1500 1/s, selected in a range that has been observed previously for bioprostheses, was introduced to the simulations to mimic viscous damping effects of surrounding fluid.

The objective of the optimization procedure was minimization of Smax defined based on the following equation: strain-stress, Smax, are defined based on the following equation:

$$S_{max} = \sqrt{S_{systole}^2 + S_{diastole}^2}$$

Where $S_{systole}$ and $S_{diastole}$ were the maximum Von Mises stress at the peak of systole and the peak diastolic pressure, respectively. It was contemplated that to reduce the bending stress on valve leaflets, including tensile and compressive stresses, most appropriate objective value to be minimized in the optimization procedure would be the maximum Von Mises stress values; therefore, the optimization procedure was run with the aim of minimizing those values.

Turning back to FIG. 2, after the large deformation analysis of the 3D TAV model under physiological loading (as shown in step 207), the output of the file of the computational model (the ABAQUS output file, in this case), was input into MATLAB again in step 208, this time to extract the stress values.

Then, at step 210, the maximum Von Mises stress values were used as an input to an algorithmic method known as a "particle swarm optimization method," which is a built-in algorithm in Isight (a process integration and design optimization software framework developed by Dassault Systémes), was used in the optimization procedure. Range of design parameters for two TAV sizes (23 mm and 26 mm, as previously described) is listed in Table 2. In the presently described experiment, approximately 500 iterations were required to reach convergence toward an optimized shape for reduction of Von Mises stresses for each one of the TAV sizes.

TABLE 2

Range of design parameters in the optimization procedure.

| Parameters | H(mm) | h(mm) | $X_f$(mm) | $Y_f$(mm) | $X_s$(mm) | $Y_s$(mm) |
|---|---|---|---|---|---|---|
| D = 23 mm | 10.3~12.3 | 7.0~9.0 | 9.0~12.7 | 0.0~1.0 | 7.0~11.0 | 0.0~6.0 |
| D = 26 mm | 14.0~16.0 | 10.0~12.5 | 9.0~12.7 | 0.0~1.0 | 7.0~11.0 | 0.0~6.0 |

Figure 5A:
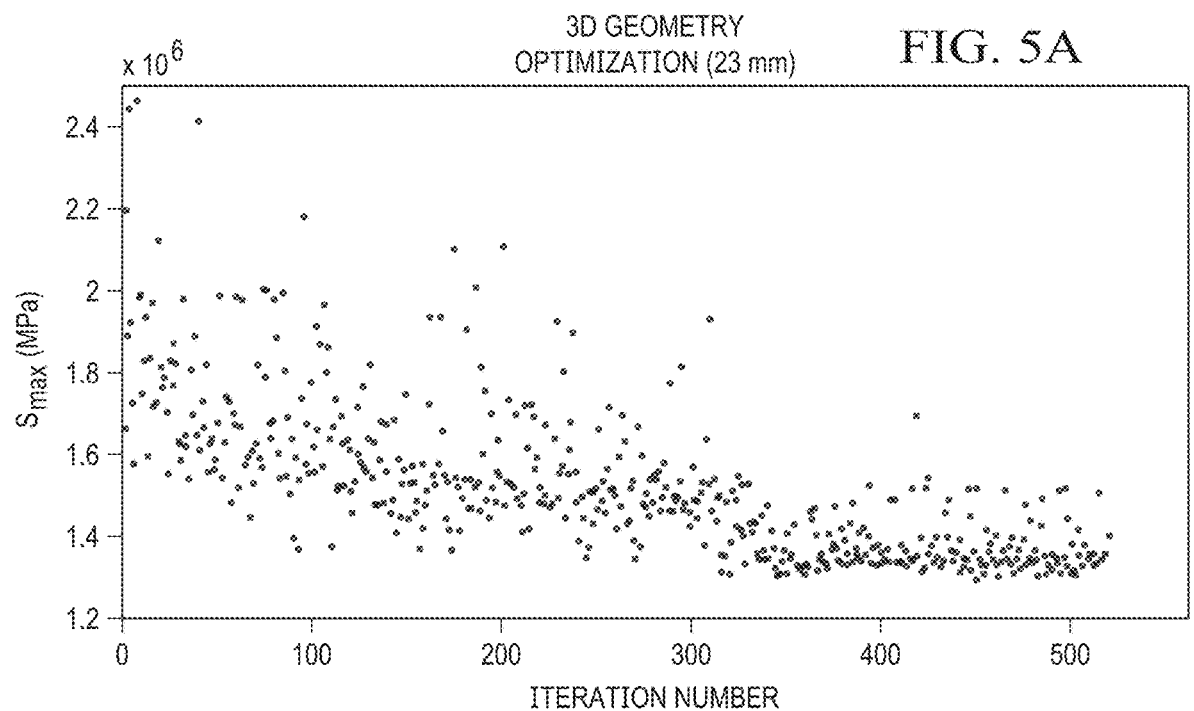
FIG. 5A shows an overview of the optimization process depicted in graphical form, wherein the square root of maximum von Mises stress ($S_{max}$) decreases as a number of iterations increases for a model of a 23 mm replacement valve.

FIG. 5A shows a graph, for a model of a 23 mm TAV, of $S_{max}$ and how it converged over the number of iterations as the particle swarm optimization method ran using the ranges of the six design parameters shown in Table 2 above. As shown, over the 500 iterations, the model increasingly converged on parameter values that resulted in low Von Mises stress values.

Figure 5B:
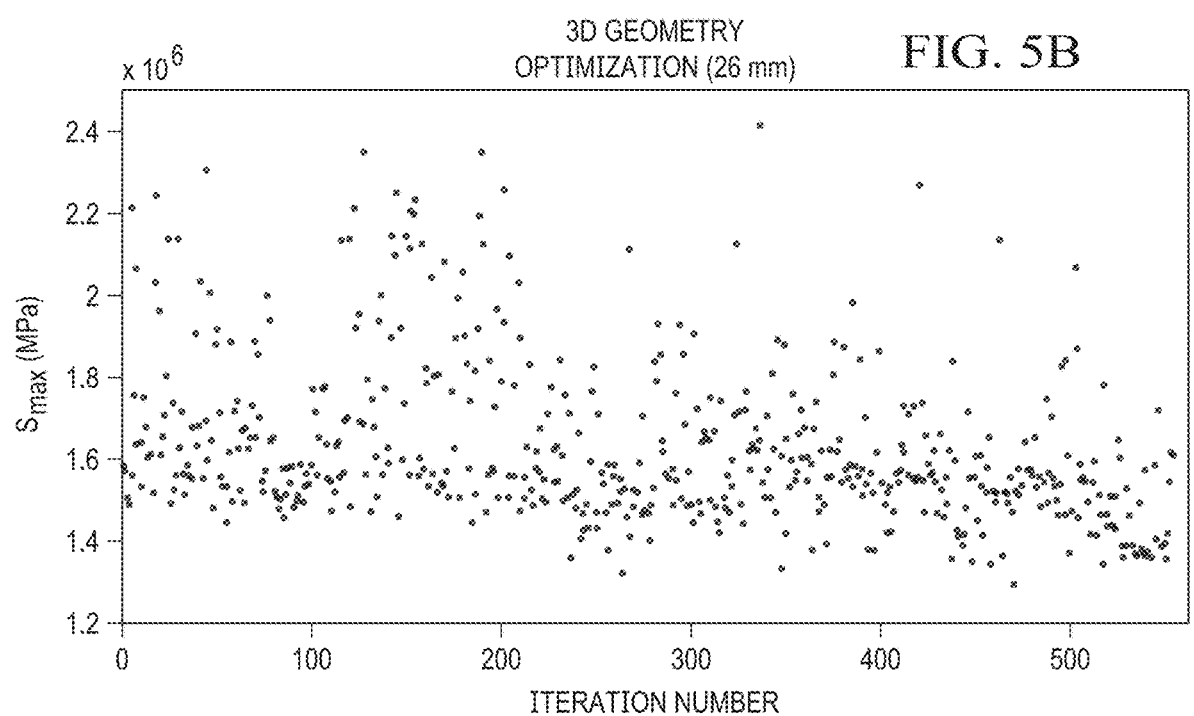
FIG. 5B shows an overview of the optimization process depicted in graphical form, wherein the square root of maximum von Mises stress ($S_{max}$) decreases as a number of iterations increases for a model of a 26 mm replacement valve.

FIG. 5B shows a graph, for a model of a 26 mm TAV, of $S_{max}$ and how it converged over the number of iterations as the particle swarm optimization method ran using the ranges of the six design parameters shown in Table 2 above. As shown, over the 500 iterations, the model increasingly converged on parameter values that resulted in low Von Mises stress values, though more variable combinations resulted in relatively high Von Mises stress values in comparison to the optimization method shown in FIG. 5A. The results shown in FIGS. 5A and 5B will be discussed in greater detail later in this disclosure.

Another aspect of the study involved a comparison with the commercially available bioprosthetic heart valves. After completing the optimization procedure, the optimized 23-mm and 26-mm leaflet geometries were compared with comparable size Carpentier-Edwards PERIMOUNT Magna surgical bioprostheses. In addition, the 26-mm optimized leaflet geometry was compared with 26-mm Edwards SAPIEN 3 transcatheter heart valve. To compare leaflet stress distribution, a 3-D generalized anisotropic Fung-type hyperelastic material model was used to characterize the anisotropic behavior of the leaflets. The strain-energy function determines relationship between stress and strain A generalized Fung strain-energy function in 3-D space is in the form:

$$\Psi = \frac{c}{2}(e^Q - 1) + \frac{1}{\mathcal{D}}\left(\frac{J_{el}^2 - 1}{2} - \ln J_{el}\right)$$

where $\Psi$ is the strain energy per unit of reference volume. D and c describe the temperature-dependent material parameters, $J_{el}$ stands for the elastic volume ratio which is equal to J in the absence of thermal strains, and Q is given by:

$$Q = E:(\mathbb{b}E)$$

where $\mathbb{b}$ is a non-dimensional symmetric fourth-order tensor of anisotropic material constants, and E is the Green-Lagrange strain tensor, under the assumption of tissue incompressibility. Considering the incompressibility assumption ($J_{el}=1$), the Fung strain energy function is reduced to:

$$\Psi = \frac{c}{2}(e^Q - 1)$$

The number of components which must be determined is similar to the elasticity tensor, namely 21 independent components for a 3-D generalized anisotropic Fung strain-energy function as shown below:

$$\mathbb{b}_{anisotropic} = \begin{bmatrix} b_{1111} & b_{1122} & b_{1133} & b_{1123} & b_{1113} & b_{1112} \\ & b_{2222} & b_{2233} & b_{2223} & b_{2213} & b_{2212} \\ & & b_{3333} & b_{3323} & b_{3313} & b_{3312} \\ & & & b_{2323} & b_{1323} & b_{1223} \\ & & \text{Symmetric} & & b_{1313} & b_{1213} \\ & & & & & b_{1212} \end{bmatrix}$$

The following material coefficients previously reported in the literature for the bioprostheses were considered in this study.

$$\mathbb{b}_{23mm-PERIMOUNT\ Magna} = \begin{bmatrix} 62.95 & 36.39 & 54.14 & 17.13 & 45.45 & 41.72 \\ & 61.88 & 45.64 & 68.15 & 67.97 & 23.42 \\ & & 65.98 & 38.70 & 63.95 & 56.17 \\ & & & 14.40 & 16.26 & 27.56 \\ & & \text{Symmetric} & & 42.57 & 17.61 \\ & & & & & 60.66 \end{bmatrix}$$

$$\mathbb{b}_{25mm-PERIMOUNT\ Magna} = \begin{bmatrix} 63.42 & 31.84 & 51.29 & 17.37 & 49.02 & 39.39 \\ & 63.74 & 46.75 & 68.38 & 63.09 & 19.22 \\ & & 62.82 & 38.51 & 60.17 & 55.50 \\ & & & 14.30 & 15.47 & 28.04 \\ & & \text{Symmetric} & & 47.30 & 13.69 \\ & & & & & 67.53 \end{bmatrix}$$

$$\mathbb{b}_{26mm-SAPIEN\ 3} = \begin{bmatrix} 87.45 & 37.88 & 56.25 & 18.49 & 45.47 & 37.23 \\ & 83.97 & 43.50 & 70.21 & 71.65 & 25.72 \\ & & 89.93 & 43.70 & 62.41 & 58.98 \\ & & & 13.92 & 15.12 & 27.96 \\ & & \text{Symmetric} & & 43.54 & 16.47 \\ & & & & & 68.56 \end{bmatrix}$$

In addition, the estimated values for c are presented in Table 3.

TABLE 3

Material parameter for the 3D anisotropic Fung models.

| Bioprosthesis | c(kPa) |
|---|---|
| 23-mm PERIMOUNT Magna | 24.62 |
| 25-mm PERIMOUNT Magna | 90.72 |
| 26-mm SAPIEN 3 | 47.53 |

For the surgical bioprostheses, a flexible frame with a uniform diameter (0.89 mm) and density (8,300 kg/m3) was considered in the FE simulations. The Young's modulus of the frame was 18.9 GPa and the Poison's ratio was 0.226. To compare the leaflet stress distribution between the commercially available bioprostheses and the optimized leaflet geometry, it was assumed that the leaflets have identical mechanical properties and thickness in each pair of comparisons. Contours of maximum in-plane principal stress of the leaflets were then determined at an identical pressure gradient across the valve (i.e., 16 kPa~120 mmHg). To avoid the mesh density sensitivity, the number of elements in the FE simulations were comparable for each pair of comparison groups.

The objective of the optimization procedure was to minimize the square root of maximum Von Mises stress (Smax) on the TAV leaflets. As shown in FIGS. 5A and 5B, there was a significant difference in the magnitude of Smax within the design domain. The maximum value of Smax was 2.46 and 2.41 MPa, while the minimum value of Smax was 1.30 and 1.29 MPa for the 23-mm (FIG. 5A) and 26-mm (FIG. 5B) TAVs, respectively. Smax reached to its minimum value after 451 and 477 iterations for 23-mm TAV (FIG. 5A) and 26-mm TAV (FIG. 5B), respectively. The minimum value of Sm, hereafter referred to as the best leaflet design, was 47.2% and 46.5% less than maximum value of Smax, hereafter referred to as the worst leaflet design, for the 23-mm and 26-mm TAVs, respectively. In addition, for the best and the worst leaflet design configurations, the maximum Von Mises stress at the peak of systole (S systole) and peak of diastolic pressure (S diastole) are listed in Table 4.

TABLE 4

The maximum Von Mises stress at the peak of systole and peak of diastolic pressure for the best and worst TAV leaflet designs.

| | $S_{systole}$(MPa) | $S_{diastole}$(MPa) | $S_{max}$(MPa) |
|---|---|---|---|
| 23-mm TAV (best leaflet design) | 0.92 | 0.91 | 1.30 |
| 23-mm TAV (worst leaflet design) | 1.22 | 2.14 | 2.46 |
| 26-mm TAV (best leaflet design) | 0.97 | 0.86 | 1.29 |
| 26-mm TAV (worst leaflet design) | 1.02 | 2.19 | 2.41 |

The optimization parameters of the best leaflet design for the 23-mm and 26-mm TAVs are listed in Table 5.

TABLE 5

Optimization parameters of the best leaflet design for the 23-mm and 26-mm TAVs.

| | H(mm) | h(mm) | $X_f$(mm) | $Y_f$(mm) | $X_s$(mm) | $Y_s$(mm) |
|---|---|---|---|---|---|---|
| 23-mm TAV, best leaflet design | 12.245 | 7.316 | 12.598 | 0.230 | 7.133 | 4.001 |
| 26-mm TAV, best leaflet design | 15.666 | 10.170 | 11.881 | 0.145 | 10.287 | 0.348 |

Figure 6A:
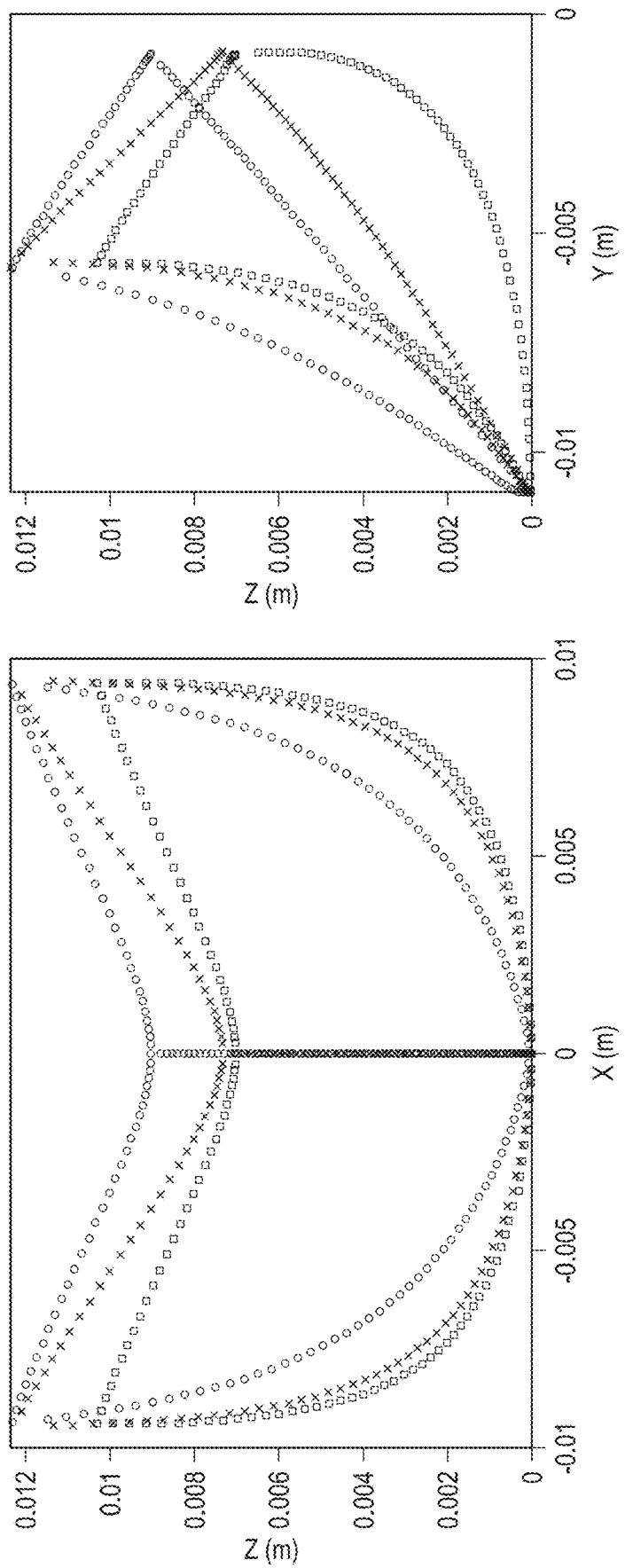
FIG. 6A is a schematic plot of the fixed-boundary edge, free-edge, and symmetric curves for the best leaflet designs with respect to the lower and upper optimization boundaries for a 23-mm replacement valve.

Moreover, the fixed-edge, free-edge and symmetry curves for the best leaflet design were plotted in FIG. 6A for the 23 mm TAV size and FIG. 6B for the 26 mm TAV size. The leaflet designs were compared with the upper and lower bound design parameters in the design space.

Figure 7A:
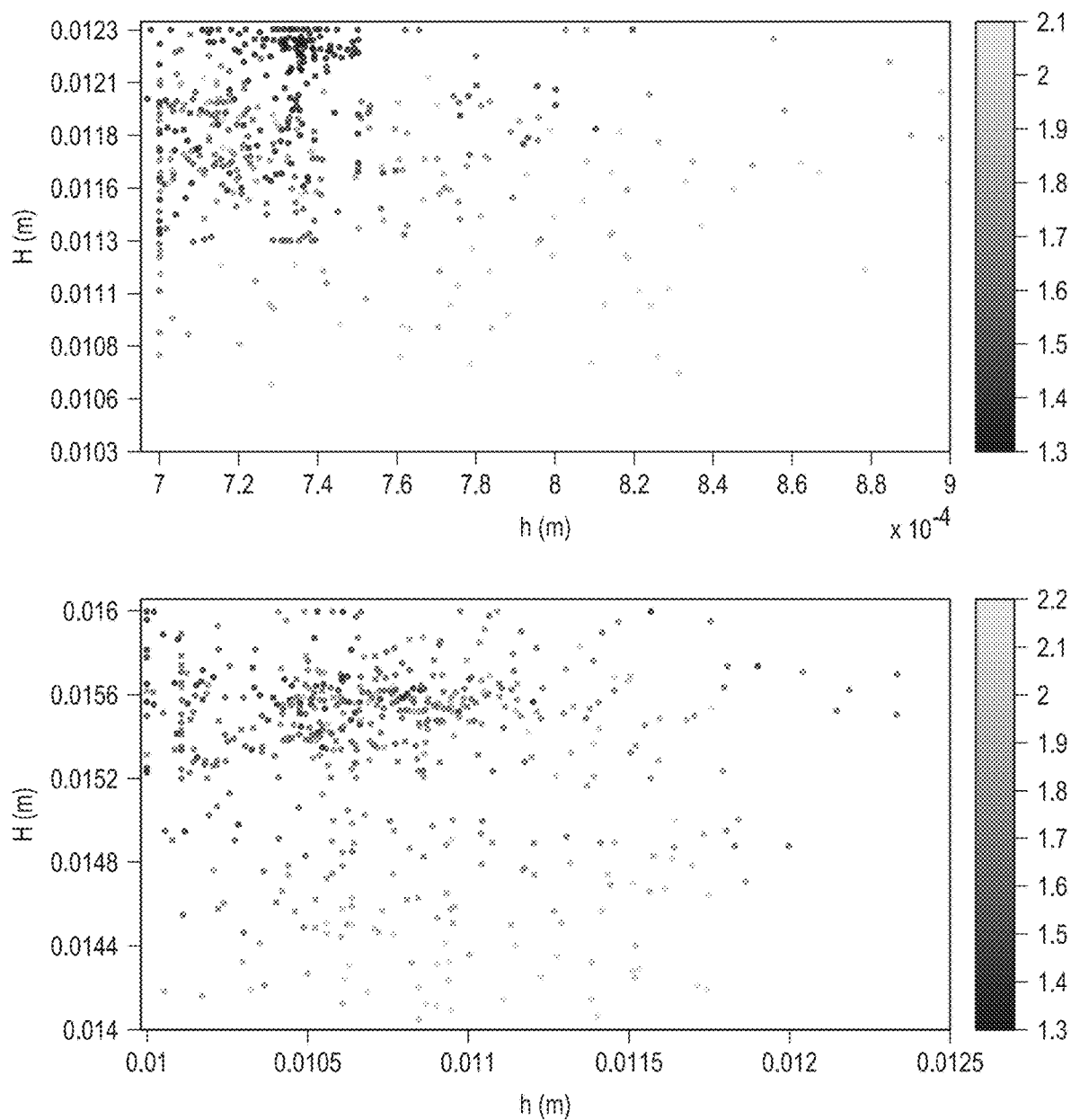
FIG. 7A shows two heat maps plotted to show the relationship between the square root of maximum Von Mises stress ($S_{max}$) and (A) valve height and leaflet coaptation height (H and h), the stress unit of the heat maps being measured in MPa.
Figure 7B:
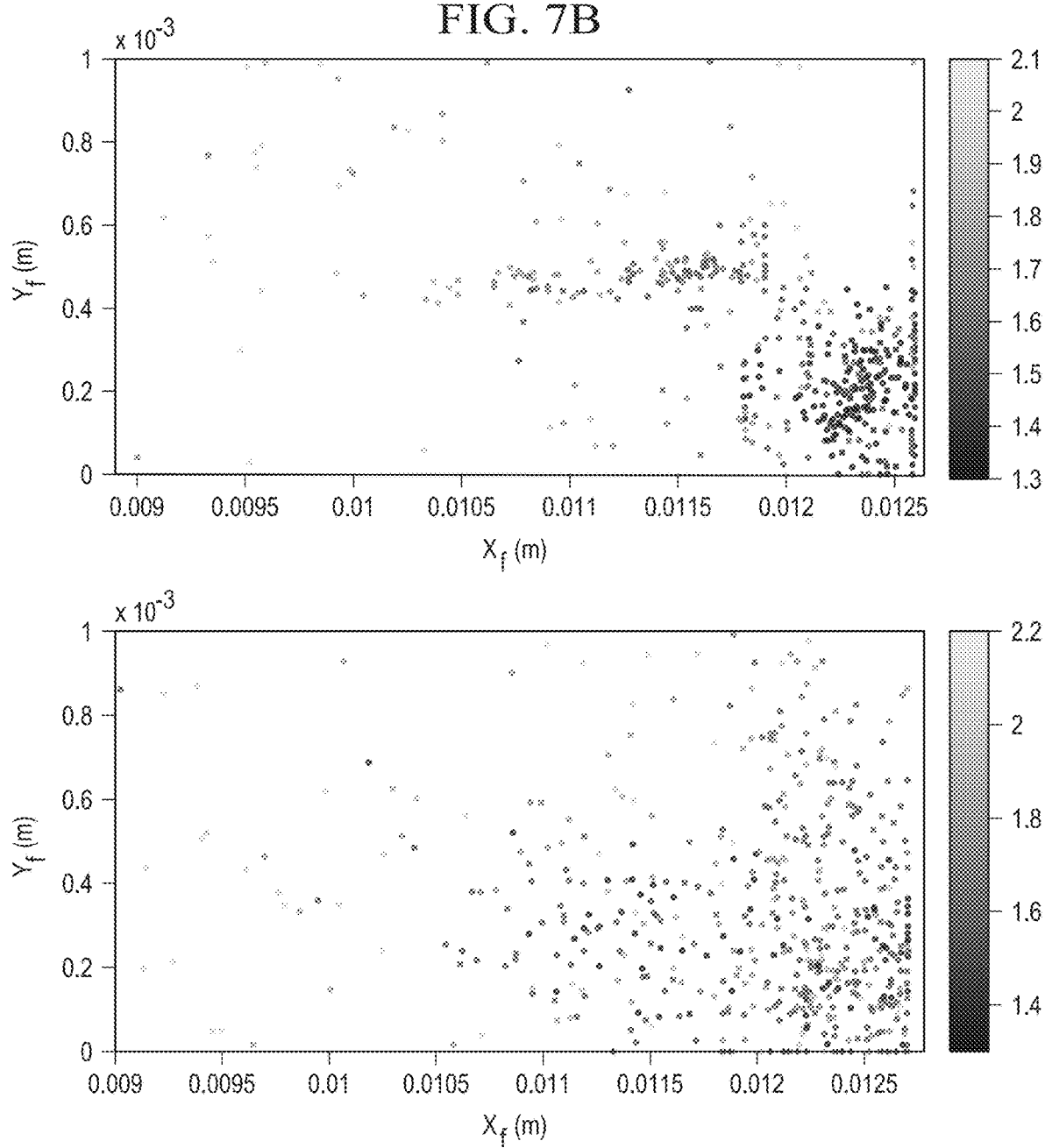
FIG. 7B shows two heat maps plotted to show the relationship between control points of B-spline 2 that controls the fixed-boundary edge ($X_f$ and $Y_f$.), the stress unit of the heat maps being measured in Mpa.
Figure 7C:
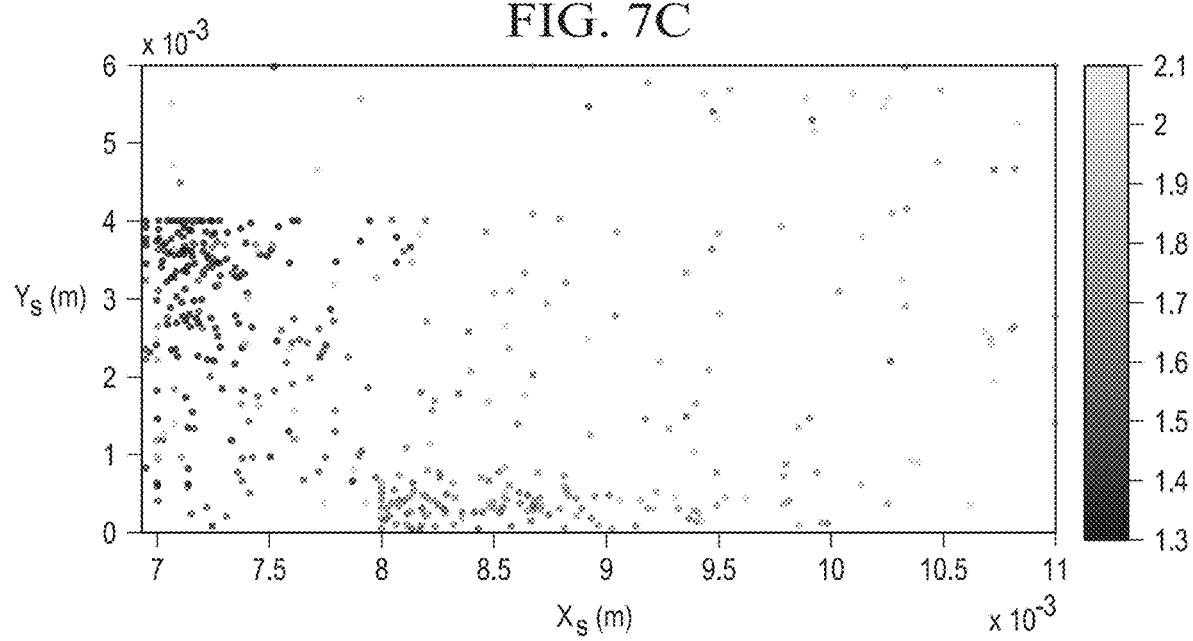
FIG. 7C control points of B-spline 1 in the plane of symmetry ($X_s$ and $Y_s$), the stress unit of the heat maps being measured in MPa.
Figure 7C:
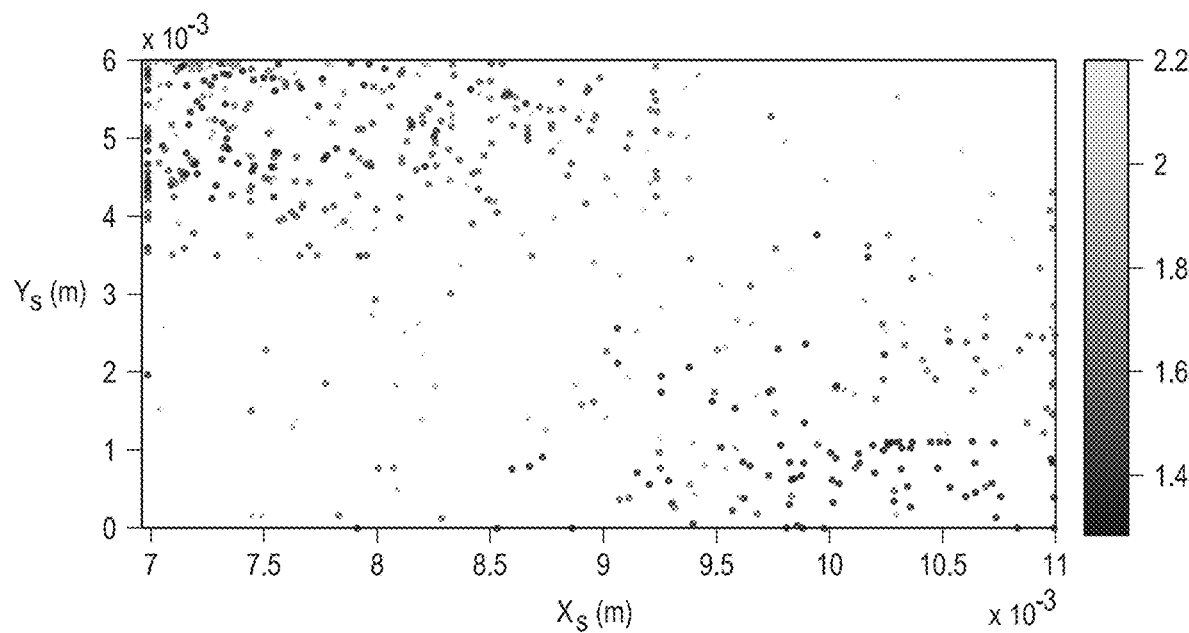

To evaluate the impact of the design parameters on the maximum Von Mises stress, correlation between the design parameters and Smax was determined for the 23-mm and 26-mm TAVs. As depicted in FIGS. 7A-C, the square root of maximum Von Mises stress (Smax) were plotted against combinations of (H, h: valve height and leaflet coaptation height) in FIG. 7A, (X f, Yf: control points of B-spline 2 that controls the fixed-boundary edge) in FIG. 7B, and (X s, Ys: control points of B-spline 1 in the plane of symmetry) in FIG. 7C. As shown in FIG. 7A, increasing the ratio of valve height (H) to leaflet coaptation height (h) decreases the square root of maximum Von Mises stress, Smax, for both 23-mm and -26 mm TAVs. In addition, as shown in FIG. 7B, as the ratio of Yf/X f was reduced for fixed boundary edge (B-Spline 2), the square root of maximum Von Mises stress, Smax, was diminished for both 23-mm and -26 mm TAV sizes. This means that increasing the curvature of the fixed-boundary edge could potentially reduce the square root of maximum Von Mises stress of the TAV leaflets. For B-spline 1 in the plane of symmetry, however, such a correlation was not observed in the design space, as shown in FIG. 7C.

Figure 8A:
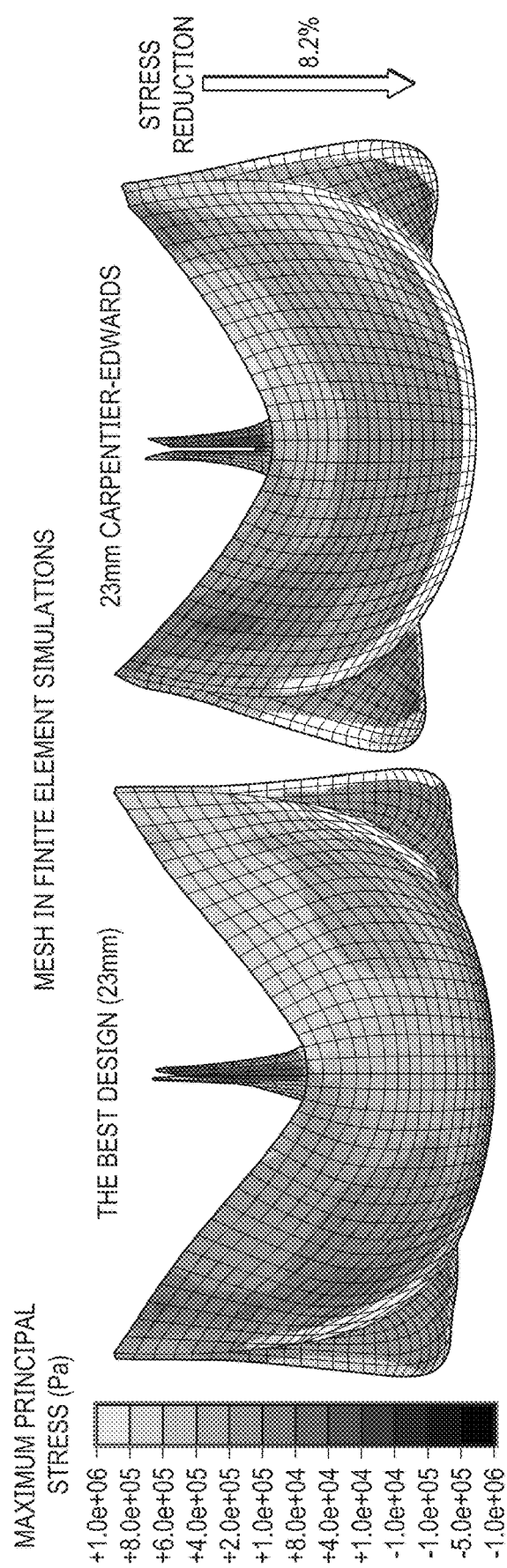
FIGS. 8 A-C illustrate comparisons of leaflet stress distribution between commercially available bioprostheses and optimized modeled leaflet design configurations according to the present disclosure.
Figure 8B:
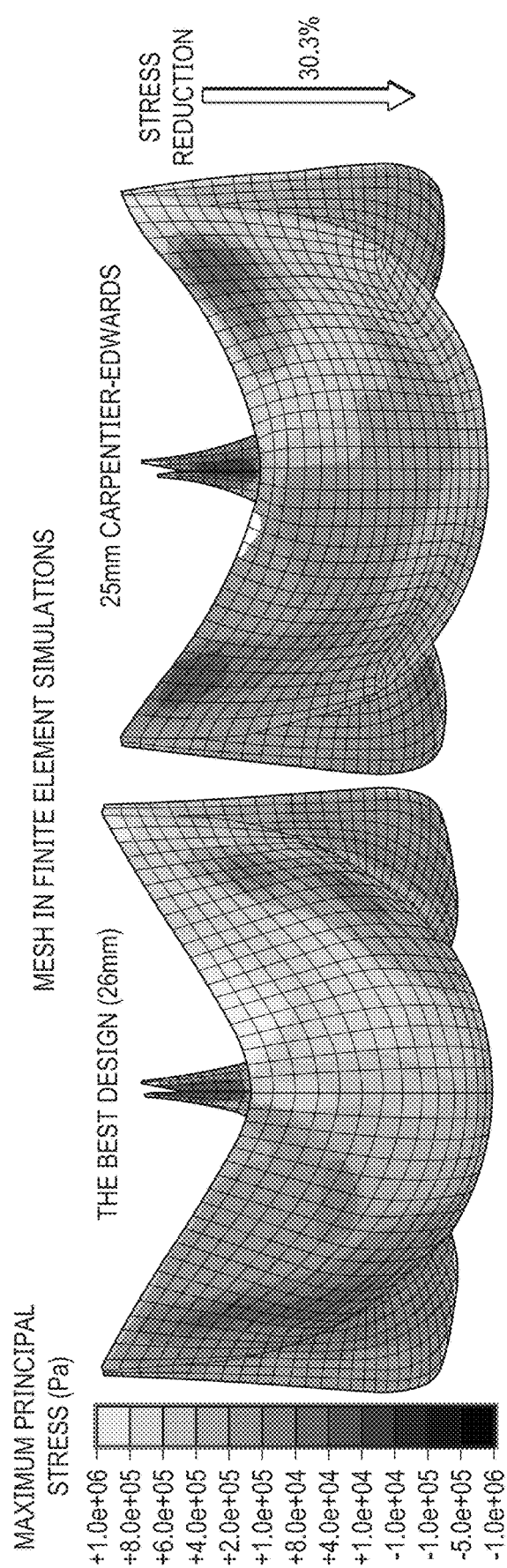
Figure 8C:
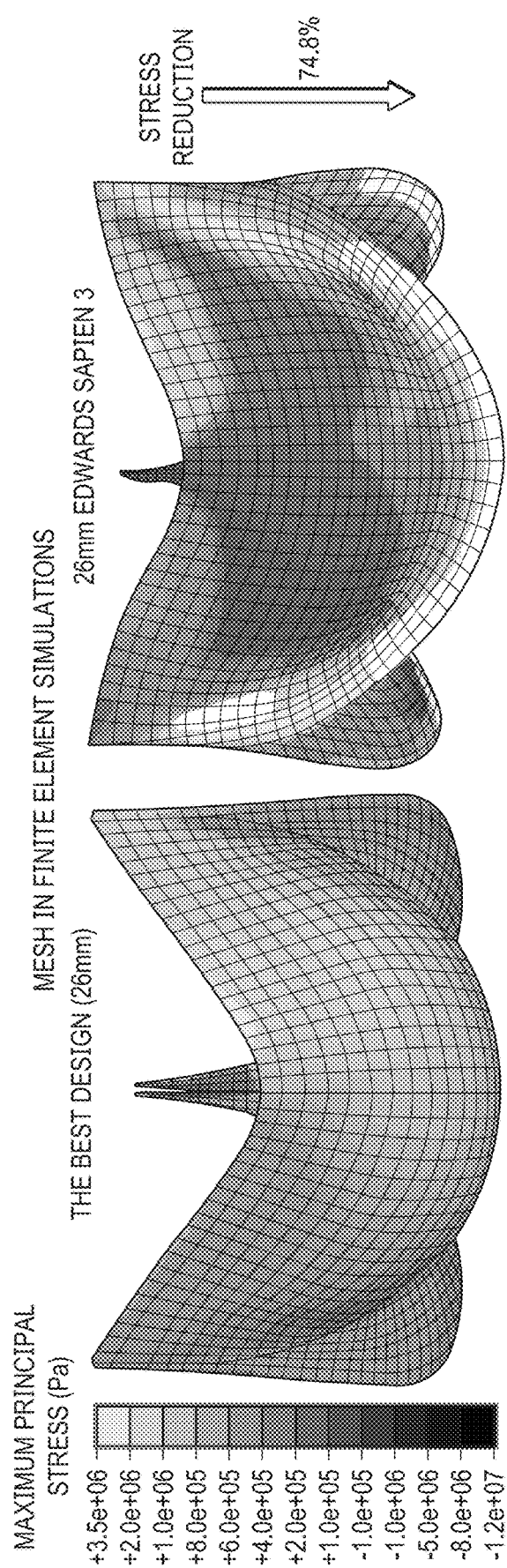

After completing the optimization procedure, to compare leaflet stress distribution between the commercially available bioprostheses and the best leaflet design configuration, contours of the maximum in-plane principal stress of the leaflets were obtained and presented in FIG. 8A-C, which show contours of the maximum in-plane principal stress of (FIG. 8A) 23-mm Carpentier-Edwards PERIMOUNT Magna versus the best TAV leaflet design with nominal size of 23 mm (FIG. 8B) 25-mm Carpentier-Edwards PERIMOUNT Magna versus the TAV leaflet design with nominal size of 26 mm (FIG. 8C) 26-mm Edward SAPIEN 3 versus the best TAV leaflet design with nominal size of 26 mm.

As shown in FIG. 8A, high stress regions were observed close to the commissures. The peak leaflet stress value for the 23-mm Carpentier-Edwards with a flexible frame reached to 0.98 MPa. However, the maximum in-plane stress of the best leaflet design with rigid stent was 0.9 MPa. In other words, there was an 8.2% reduction in the peak in-plane maximum principal stress in the optimized TAV geometry. An identical uniform thickness of 0.5 mm and material property were considered for the two models. Stress in the belly region was also lower in the best leaflet design than the 23-mm Carpentier-Edwards PERIMOUNT Magna surgical bioprosthesis.

A similar trend was observed with the 26-mm TAV (FIG. 8B). The maximum in-plane stress of the best leaflet design with rigid frame was 0.69 MPa, while the maximum in-plane stress for the 25-mm Carpentier-Edwards PERIMOUNT Magna surgical bioprosthesis with flexible frame was 0.99 MPa. In other words, there was a 30.3% reduction in the peak in-plane maximum principal stress in the optimized TAV geometry. Both models had an identical leaflet thickness of 0.56 mm and leaflet mechanical properties. Stress in the belly and commissure regions was lower in the best leaflet design compared to the 25-mm Carpentier-Edwards PERIMOUNT Magna surgical bioprosthesis (FIG. 8B). Lastly, the optimized 26-mm TAV was compared with 26-mm Edwards SAPIEN 3 with rigid frame (FIG. 8C). Identical material property and leaflet thickness (0.32 mm) were considered for the two models. The in-plane stress distribution of the optimized geometry was considerably different from that of the 26-mm Edwards SAPIEN 3 (FIG. 8C). A peak leaflet stress of 0.86 MPa was found in the best design of TAV 26 mm close the fixed boundary edge. However, the peak in-plane maximum principal stress for the SAPIEN 3 was 3.42 MPa close to the commissures. In other words, there was an 74.8% reduction in the peak in-plane maximum principal stress in the optimized TAV geometry.

The study discussed in the present disclosure provides an automated optimization framework to reduce TAV leaflet stress under dynamic physiological loading condition. Commercially available software packages such as MATLAB, SolidWorks, and ABAQUS/Explicit were linked together using Isight to develop the optimization framework. In addition, particle swarm optimization method was used to examine and explore the design space to obtain optimized leaflet geometry for 23-mm and 26-mm TAVs. The optimized leaflet designs were compared with two commercially available bioprostheses, i.e., Carpentier-Edwards PERIMOUNT Magna surgical bioprosthesis and Edwards SAPIEN 3 transcatheter heart valve. A considerable reduction in the peak maximum in-plane principal stress was observed in the optimized TAV geometries than the commercially available bioprostheses.

During the past couple of years, a few computational frameworks has been developed to optimize the design of bioprosthetic aortic valves leaflets to minimize the peak stress within the leaflets and achieve a better hemodynamic performance. Recently, researchers (Li and Sun, 2017 Li, K., Sun, W., 2017. Simulated transcatheter aortic valve deformation: a parametric study on the impact of leaflet geometry on valve peak stress. International journal for numerical methods in biomedical engineering 33 (3), e02814.) performed an optimization framework to assess the impact of TAV leaflet geometry on the leaflet stress distribution and to minimize its peak stress in both circular and elliptical configurations. In the study, all initial 3D TAV geometries were generated from 2D leaflet designs and were virtually assembled automatically in ABAQUS using a Python script. A semilunar shaped 2D leaflet design consists of one leaflet-stent attachment edge and one free edge that were parameterized by two exponential functions. The computational parametric study was carried out to minimize the peak maximum principal stress on the leaflets under quasi static pressure loading. The authors found a range of leaflet peak stress between 0.87 MPa and 2.77 MPa under the nominal circular configuration.

The peak stress on the optimal leaflet design was 5% lower than the nominal design derived from a previous study done by the same researchers (Li and Sun, 2010 Li, K., Sun, W., 2010. Simulated thin pericardial bioprosthetic valve leaflet deformation under static pressure-only loading conditions: implications for percutaneous valves. Ann. Biomed. Eng. 38 (8), 2690-2701.). In addition, the analysis showed that increasing the free edge width had the highest overall impact on decreasing the peak stress value of the leaflets (Li and Sun, 2017). In a separate parametric study, Xu and colleagues (Xu et al., 2017 Xu, F., Morganti, S., Zakerzadeh, R., Kamensky, D., Auricchio, F., Reali, A., Hughes, T. J., Sacks, M. S., Hsu, M. C., 2017. A framework for designing patient-specific bioprosthetic heart valves using immersogeometric fluid-structure interaction analysis. International journal for numerical methods in biomedical engineering) developed a computational framework to design patient-specific bioprosthetic heart valves to analyze the impact of the leaflet's geometry on valve hemodynamics. Two NURBS curves were defined to parameterize the leaflets design, one free-edge curve and one belly-region curve. The suturing line length and shape were kept constant and fixed in the study. By changing the location of two control points of the NURBS curves, the valve design was parametrically and manually altered. The study showed the potential of parametric studies to create more effective design of bioprosthetic heart valves and reduce patent-prosthesis mismatch (Xu et al., 2017).

In contrast, the present study shows an effective approach to use commercially available software and explore a vast range of leaflet shapes with only 6 parameters: valve height, leaflet coaptation height, and two control points for the fixed-edge and free-edge B-splines. The framework creates three-dimensional leaflet geometries efficiently and eliminate any residual stress that will be created by transforming 2D planer mesh into its 3D configuration, observed in previous studies (Li and Sun, 2017). A benefit of this framework is that it may determine optimized leaflet design for a wide range of TAV design parameters and control variables. In addition, it is important to determine the optimized leaflet geometry under dynamic loading condition. Simplified loading conditions, e.g. quasi-static loading in the optimization procedure, may not represent the true loading condition that the leaflets will experience following heart valve replacement in clinical practice.

In the past few decades, several computational simulations have been performed to assess stress and strain distributions of bioprosthetic heart valves. Computational modeling can provide qualitative and quantitative insights into the durability of bioprostheses. The increased mechanical stress on TAV leaflets may lead to accelerated tissue degeneration and diminished long-term valve durability. Besides leaflet geometry, there are additional factors such as TAV crimping and incomplete transcatheter aortic valve expansion that might affect the long-term durability of TAVs. Nevertheless, the results presented herein underline the opportunity to improve TAV leaflet design in the next generation of TAVs to enhance long-term durability of the bioprostheses.

Another aspect of the present disclosure is that leaflets and entire bioprosthetic valves themselves may be manufactured according to the optimized shapes designed by the models. The bioprosthetic valves may be made from bovine or porcine pericardium tissue, or any other materials that may be suitably formed into the optimized leaflet shapes designed herein.

It is contemplated that for surgical replacement valves other than TAV valves, the optimized shapes of the leaflets may of course vary in comparison to the optimized shapes shown herein.

In summary, the present disclosure provides an automatic computational framework using commercially available software to optimize the TAV leaflet shape under physiological loading conditions. Optimized leaflet designs for two different TAV sizes (23-mm and 26-mm) were obtained using particle swarm optimization algorithm. Furthermore, the impact of leaflet design parameters was evaluated on leaflet maximum stress. The results showed that increasing the ratio of valve height to leaflet coaptation height decreases the maximum Von Mises stress of the leaflets. Furthermore, increasing the curvature of the fixed-boundary edge could potentially reduce the maximum stress of the TAV leaflets.

In addition, the optimized leaflet designs were compared with Carpentier-Edwards PERIMOUNT Magna surgical bioprostheses and Edwards SAPIEN 3 transcatheter heart valve. A considerable reduction in the peak in-plane maximum principal stress was observed in the optimized TAV geometry in comparison to the commercially available bioprosthetic heart valves. The framework of the present disclosure may be used to determine optimized leaflet design for a wide range of TAV design parameters and control variables (e.g., different frame designs and leaflet properties). The framework may also be used to determine optimized leaflet design in other surgical replacement valves. Such improved leaflet design in surgical valves provides the benefits of increasing long-term durability in patients.

Figure 9:
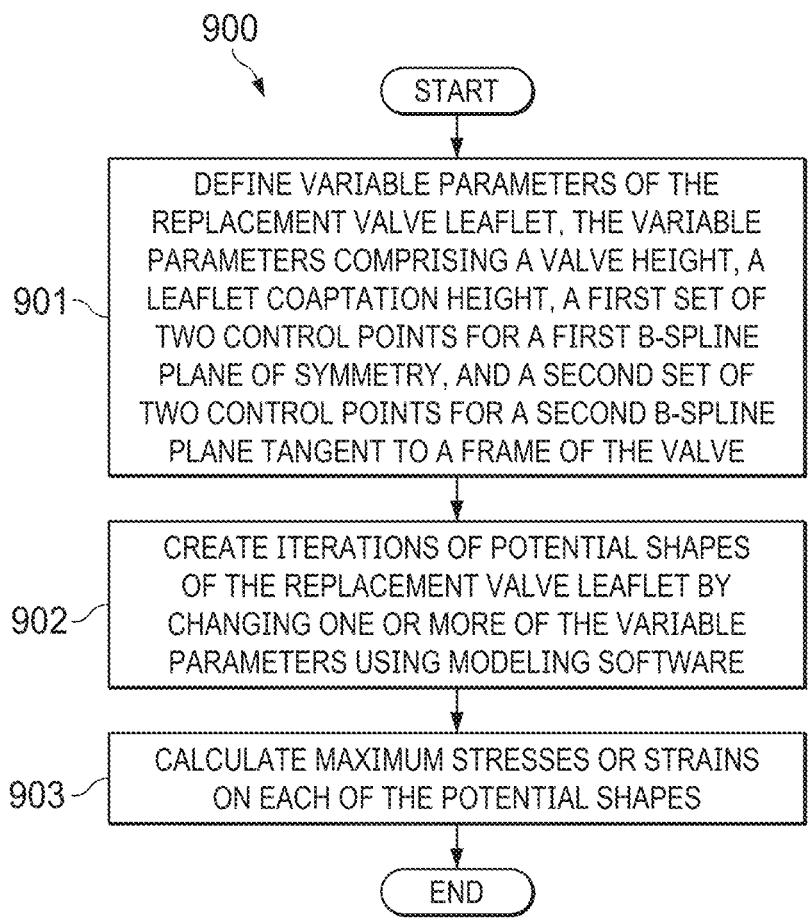
FIG. 9 is a flowchart showing a method of the present disclosure.
Figure 10:
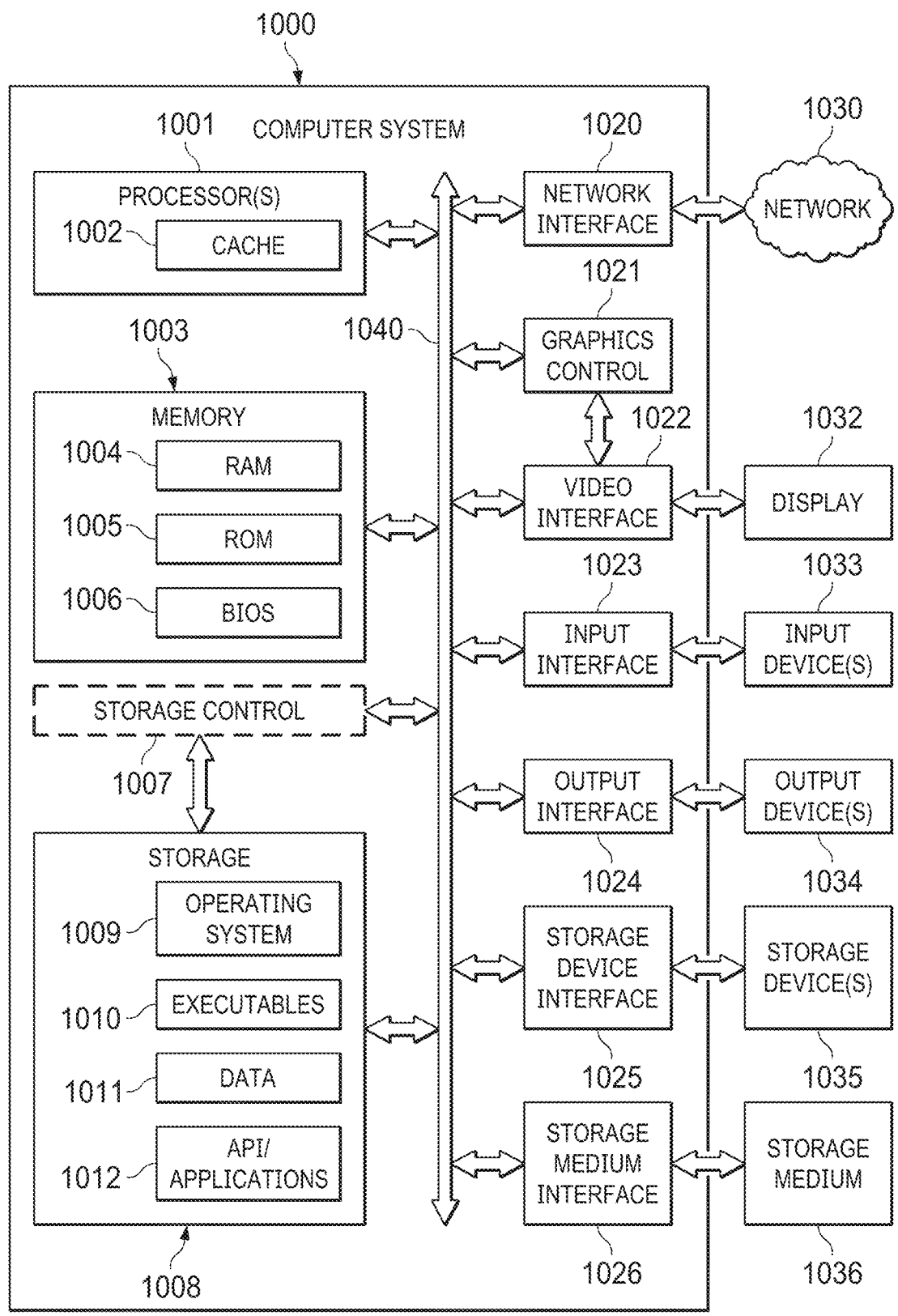
FIG. 10 is a diagram of a computing device that may be used to implement one or more aspects of the present disclosure.

FIG. 9 shows a method 900 for creating an optimized shape for a replacement valve leaflet. The method may comprise, at step 901, defining variable parameters of the replacement valve leaflet, the variable parameters comprising a valve height; a leaflet coaptation height, a first set of two control points for a first B-spline plane of symmetry; and a second set of two control points for a second B-spline plane tangent to a frame of the valve. The method may then comprise, at step 902, creating iterations of potential shapes of the replacement valve leaflet by changing one or more of the variable parameters using modeling software. Then, the method may comprise, at step 903, calculating maximum stresses or strains on each of the potential shapes. Referring next to FIG. 10, it is a block diagram depicting an exemplary machine that includes a computer system 1000 within which a set of instructions can execute for causing a device to perform or execute any one or more of the aspects and/or methodologies of the present disclosure. The components in FIG. 10 are examples only and do not limit the scope of use or functionality of any hardware, software, embedded logic component, or a combination of two or more such components implementing particular embodiments.

Computer system 1000 may include a processor 1001, a memory 1003, and a storage 1008 that communicate with each other, and with other components, via a bus 1040. The bus 1040 may also link a display 1032, one or more input devices 1033 (which may, for example, include a keypad, a keyboard, a mouse, a stylus, etc.), one or more output devices 1034, one or more storage devices 1035, and various tangible storage media 1036. All of these elements may interface directly or via one or more interfaces or adaptors to the bus 1040. For instance, the various tangible storage media 1036 can interface with the bus 1040 via storage medium interface 1026. Computer system 1000 may have any suitable physical form, including but not limited to one or more integrated circuits (ICs), printed circuit boards (PCBs), mobile handheld devices (such as mobile telephones or PDAs), laptop or notebook computers, distributed computer systems, computing grids, or servers.

Processor(s) 1001 (or central processing unit(s) (CPU(s))) optionally contains a cache memory unit 1002 for temporary local storage of instructions, data, or computer addresses. Processor(s) 1001 are configured to assist in execution of computer readable instructions. Computer system 1000 may provide functionality for the components depicted in FIG. 1 as a result of the processor(s) 1001 executing non-transitory, processor-executable instructions embodied in one or more tangible computer-readable storage media, such as memory 1003, storage 1008, storage devices 1035, and/or storage medium 1036. The computer-readable media may store software that implements particular embodiments, and processor(s) 1001 may execute the software. Memory 1003 may read the software from one or more other computer-readable media (such as mass storage device(s) 1035, 1036) or from one or more other sources through a suitable interface, such as network interface 1020. The software may cause processor(s) 1001 to carry out one or more processes or one or more steps of one or more processes described or illustrated herein. Carrying out such processes or steps may include defining data structures stored in memory 1003 and modifying the data structures as directed by the software.

The memory 1003 may include various components (e.g., machine readable media) including, but not limited to, a random access memory component (e.g., RAM 1004) (e.g., a static RAM "SRAM", a dynamic RAM "DRAM, etc.), a read-only component (e.g., ROM 1005), and any combinations thereof. ROM 1005 may act to communicate data and instructions unidirectionally to processor(s) 1001, and RAM 1004 may act to communicate data and instructions bidirectionally with processor(s) 1001. ROM 1005 and RAM 1004 may include any suitable tangible computer-readable media described below. In one example, a basic input/output system 1006 (BIOS), including basic routines that help to transfer information between elements within computer system 1000, such as during start-up, may be stored in the memory 1003.

Fixed storage 1008 is connected bidirectionally to processor(s) 1001, optionally through storage control unit 1007. Fixed storage 1008 provides additional data storage capacity and may also include any suitable tangible computer-readable media described herein. Storage 1008 may be used to store operating system 1009, EXECs 1010 (executables), data 1011, API applications 1012 (application programs), and the like. Often, although not always, storage 1008 is a secondary storage medium (such as a hard disk) that is slower than primary storage (e.g., memory 1003). Storage 1008 can also include an optical disk drive, a solid-state memory device (e.g., flash-based systems), or a combination of any of the above. Information in storage 1008 may, in appropriate cases, be incorporated as virtual memory in memory 1003.

In one example, storage device(s) 1035 may be removably interfaced with computer system 1000 (e.g., via an external port connector (not shown)) via a storage device interface 1025. Particularly, storage device(s) 1035 and an associated machine-readable medium may provide nonvolatile and/or volatile storage of machine-readable instructions, data structures, program modules, and/or other data for the computer system 1000. In one example, software may reside, completely or partially, within a machine-readable medium on storage device(s) 1035. In another example, software may reside, completely or partially, within processor(s) 1001.

Bus 1040 connects a wide variety of subsystems. Herein, reference to a bus may encompass one or more digital signal lines serving a common function, where appropriate. Bus 1040 may be any of several types of bus structures including, but not limited to, a memory bus, a memory controller, a peripheral bus, a local bus, and any combinations thereof, using any of a variety of bus architectures. As an example and not by way of limitation, such architectures include an Industry Standard Architecture (ISA) bus, an Enhanced ISA (EISA) bus, a Micro Channel Architecture (MCA) bus, a Video Electronics Standards Association local bus (VLB), a Peripheral Component Interconnect (PCI) bus, a PCI-Express (PCI-X) bus, an Accelerated Graphics Port (AGP) bus, HyperTransport (HTX) bus, serial advanced technology attachment (SATA) bus, and any combinations thereof.

Computer system 1000 may also include an input device 1033. In one example, a user of computer system 1000 may enter commands and/or other information into computer system 1000 via input device(s) 1033. Examples of an input device(s) 1033 include, but are not limited to, an alpha-numeric input device (e.g., a keyboard), a pointing device (e.g., a mouse or touchpad), a touchpad, a joystick, a gamepad, an audio input device (e.g., a microphone, a voice response system, etc.), an optical scanner, a video or still image capture device (e.g., a camera), and any combinations thereof. Input device(s) 1033 may be interfaced to bus 1040 via any of a variety of input interfaces 1023 (e.g., input interface 1023) including, but not limited to, serial, parallel, game port, USB, FIREWIRE, THUNDERBOLT, or any combination of the above.

In particular embodiments, when computer system 1000 is connected to network 1030, computer system 1000 may communicate with other devices, specifically mobile devices and enterprise systems, connected to network 1030. Communications to and from computer system 1000 may be sent through network interface 1020. For example, network interface 1020 may receive incoming communications (such as requests or responses from other devices) in the form of one or more packets (such as Internet Protocol (IP) packets) from network 1030, and computer system 1000 may store the incoming communications in memory 1003 for processing. Computer system 1000 may similarly store outgoing communications (such as requests or responses to other devices) in the form of one or more packets in memory 1003 and communicated to network 1030 from network interface 1020. Processor(s) 1001 may access these communication packets stored in memory 1003 for processing.

Examples of the network interface 1020 include, but are not limited to, a network interface card, a modem, and any combination thereof. Examples of a network 1030 or network segment 1030 include, but are not limited to, a wide area network (WAN) (e.g., the Internet, an enterprise network), a local area network (LAN) (e.g., a network associated with an office, a building, a campus or other relatively small geographic space), a telephone network, a direct connection between two computing devices, and any combinations thereof. A network, such as network 1030, may employ a wired and/or a wireless mode of communication. In general, any network topology may be used.

Information and data can be displayed through a display 1032. Examples of a display 1032 include, but are not limited to, a liquid crystal display (LCD), an organic liquid crystal display (OLED), a cathode ray tube (CRT), a plasma display, and any combinations thereof. The display 1032 can interface to the processor(s) 1001, memory 1003, and fixed storage 1008, as well as other devices, such as input device(s) 1033, via the bus 1040. The display 1032 is linked to the bus 1040 via a video interface 1022, and transport of data between the display 1032 and the bus 1040 can be controlled via the graphics control 1021.

In addition to a display 1032, computer system 1000 may include one or more other peripheral output devices 1034 including, but not limited to, an audio speaker, a printer, and any combinations thereof. Such peripheral output devices may be connected to the bus 1040 via an output interface 1024. Examples of an output interface 1024 include, but are not limited to, a serial port, a parallel connection, a USB port, a FIREWIRE port, a THUNDERBOLT port, and any combinations thereof.

In addition, or as an alternative, computer system 1000 may provide functionality as a result of logic hardwired or otherwise embodied in a circuit, which may operate in place of or together with software to execute one or more processes or one or more steps of one or more processes described or illustrated herein. Reference to software in this disclosure may encompass logic, and reference to logic may encompass software. Moreover, reference to a computer-readable medium may encompass a circuit (such as an IC) storing software for execution, a circuit embodying logic for execution, or both, where appropriate. The present disclosure encompasses any suitable combination of hardware, software, or both.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A method for creating an optimized shape for a replacement valve leaflet, the method comprising:
defining variable parameters of the replacement valve leaflet, the variable parameters comprising:
a valve height;
a leaflet coaptation height,
a first set of two control points for a first B-spline in a plane of symmetry of the replacement valve leaflet; and
a second set of two control points for a second B-spline in a plane tangent to a frame of the valve;
creating iterations of potential shapes of the replacement valve leaflet by changing the variable parameters using modeling software;
calculating maximum stresses or strains on each of the potential shapes; and selecting one of the potential shapes with the lowest maximum stress as the optimized shape for the replacement valve leaflet.

2. The method of claim 1, further comprising:
manufacturing the replacement valve leaflet in one or more of the potential shapes created by the modeling software.

3. The method of claim 1, wherein the replacement valve leaflet is configured for use in an aortic replacement valve.

4. The method of claim 1, wherein the replacement valve leaflet is configured for use in a transcatheter replacement valve.

5. The method of claim 1, wherein the replacement valve leaflet is configured for manufacture from tissue.

6. The method of claim 1, wherein the replacement valve leaflet is configured for manufacture from polymeric material.

7. The method of claim 1, wherein the modeling software is a commercially-available modeling software.

8. The method of claim 1, wherein the replacement valve leaflet comprises at least one non-uniform rational B-splines (NURBS) curves.

9. A replacement valve leaflet, wherein an optimized shape of the replacement valve leaflet is determined by the method comprising:
defining variable parameters of the replacement valve leaflet, the variable parameters comprising:
a valve height;
a leaflet coaptation height,
a first set of two control points for a first B-spline in a plane of symmetry of the replacement valve leaflet; and
a second set of two control points for a second B-spline in a plane tangent to a frame of the valve;
creating iterations of potential shapes of the replacement valve leaflet by changing the variable parameters using modeling software;
calculating maximum stresses or strains on each of the potential shapes; and
selecting one of the potential shapes with the lowest maximum stress as the optimized shape for the replacement valve leaflet.

10. The replacement valve leaflet of claim 9, wherein the replacement valve leaflet is manufactured according to match one or more of the potential shapes created by the modeling software.

11. The replacement valve leaflet of claim 10, wherein the replacement valve leaflet is manufactured for use in an aortic replacement valve.

12. The replacement valve leaflet of claim 10, wherein the replacement valve leaflet is manufactured for use in a transcatheter replacement valve.

13. The replacement valve leaflet of claim 10, wherein the replacement valve leaflet is manufactured out of tissue.

14. The replacement valve leaflet of claim 10, wherein the replacement valve leaflet is manufactured out of polymeric material.

15. The replacement valve leaflet of claim 9, wherein the replacement valve leaflet comprises at least one non-uniform rational B-splines (NURBS) curves.

16. A non-transitory, tangible computer readable storage medium, encoded with processor readable instructions to perform a method for creating an optimized shape for a replacement valve leaflet, the method comprising:
defining variable parameters of the replacement valve leaflet, the variable parameters comprising:
a valve height;
a leaflet coaptation height,
a first set of two control points for a first B-spline in a plane of symmetry of the replacement valve leaflet; and
a second set of two control points for a second B-spline in a plane tangent to a frame of the valve;
creating iterations of potential shapes of the replacement valve leaflet by changing the variable parameters using modeling software;
calculating maximum stresses or strains on each of the potential shapes; and
selecting one of the potential shapes with the lowest maximum stress as the optimized shape for the replacement valve leaflet.

17. The non-transitory, tangible computer readable storage medium of claim 16, wherein the replacement valve leaflet is configured for use in an aortic replacement valve.

18. The non-transitory, tangible computer readable storage medium of claim 16, wherein the replacement valve leaflet is configured for use in a transcatheter replacement valve.

19. The non-transitory, tangible computer readable storage medium of claim 16, wherein the replacement valve leaflet is configured for manufacture from tissue.

20. The non-transitory, tangible computer readable storage medium of claim 16, wherein the replacement valve leaflet is configured for manufacture from polymeric material.

21. The method of claim 1, wherein the calculating includes calculating maximum stresses or strains on each of the potential shapes under dynamic physiological loading conditions.

22. The replacement valve leaflet of claim 9, wherein the calculating of the method includes calculating maximum stresses or strains on each of the potential shapes under dynamic physiological loading conditions.

23. The non-transitory, tangible computer readable storage medium of claim 16, wherein the calculating of the method includes calculating maximum stresses or strains on each of the potential shapes under dynamic physiological loading conditions.

* * * * *